United States Patent
Kapoor et al.

(10) Patent No.: US 9,663,773 B2
(45) Date of Patent: May 30, 2017

(54) RECOMBINANT MESO-ACTIVE THERMO-STABLE PROTEIN AND PROCESSES OF DESIGN AND BIOSYNTHESIS THEREOF

(71) Applicant: COUNCIL OF SCIENTIFIC & INDUSTRIAL RESEARCH, New Delhi (IN)

(72) Inventors: Divya Kapoor, Jolandhae (IN); Sanjeev Kumar Chandrayan, Bihar (IN); Shubbir Ahmed, Hewrah (IN); Swati Sharma, Malden, MA (US); Manish Datt, New Delhi (IN); Balvinder Singh, Chandigarh (IN); Karthikeyan Subramanian, Chandigarh (IN); Purnananda Guptasarma, Chandigarh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 41 days.

(21) Appl. No.: 14/715,919

(22) Filed: May 19, 2015

(65) Prior Publication Data

US 2015/0322418 A1  Nov. 12, 2015

Related U.S. Application Data

(62) Division of application No. 11/936,009, filed on Nov. 6, 2007, now Pat. No. 9,062,296.

(30) Foreign Application Priority Data

Nov. 6, 2006 (IN) .......................... 2411/DEL/2006

(51) Int. Cl.
C12N 9/00 (2006.01)
C12N 9/14 (2006.01)
C12N 9/42 (2006.01)
G06F 19/16 (2011.01)
C12N 9/96 (2006.01)
G06F 19/22 (2011.01)

(52) U.S. Cl.
CPC ............ *C12N 9/2437* (2013.01); *C12N 9/96* (2013.01); *G06F 19/16* (2013.01); *C12Y 302/01004* (2013.01); *G06F 19/22* (2013.01)

(58) Field of Classification Search
CPC .......... C12N 9/00; C12N 9/14; C12N 9/2437; C12N 15/102
See application file for complete search history.

(56) References Cited

U.S. PATENT DOCUMENTS 6,268,328 B1 * 7/2001 Mitchinson ........ C11D 3/38645
162/95

6,812,018 B2 * 11/2004 Wicher ............ C12Y 302/0100
435/183
7,139,665 B2  11/2006 Datta et al.

OTHER PUBLICATIONS

Filikov et al. 2002; Computational stabilization of human growth hormone. Protein Science. 11: 1452-1461.*
Rivera et al. 2003; alpha amylase from Bacillus licheniformis mutants near to the catalytic site: effects of hydrolytic and transglycosylation activity. Protein Engineering. 16(7): 505-514.*
Roberge et al. 1999; characterization of active-site aromatic residuces in xylanase A from Streptomyces lividans. Proteins Engineering. 12(3): 251-257.*
Nixon et al. 1999; Rational design of a scytalone dehydratase-like enzyme using a structurally homologous protein scaffold. Proc. Natl. Acad. Sci. 96: 3568-3571.*
Gerard J. Kleywegt, "Use of Non-crystallographic Symmetry in Protein Structure Refinement", Acta Cryst, 1996, D52: 842-857.
Krista L. Morley et al., "Improving enzyme properties: when are closer mutations better?", Trends in Biotechnology, 2005, 23(5): 231-237.
Mats Sandgren et al., "Comparison of family 12 glycoside hydrolases and recruited substitutions important for thermal stability", Protein Science, 2003, 12:848-860.
Mats Sandgren et al., "The X-ray Crystal Structure of the Trichoderma reesei Family 12 Endoglucanase 3, Cel12A, at 1.9 A Resolution", Journal of Molecular Biology, 2001, 308:295-310.
Susan J. Crennell et al., "The Structure of Rhodothermus marinus Cel12A, a Highly Thermostable Family 12 Endoglucanase, at 1.8 A Resolution", Journal of Molecular Biology, 2002, 320:883-897.
Holms et al., "Protein Structure Comparison by ALignment of Distance Matrices," J. Mol. Biol., 1993, vol. 233: 123-138.

(Continued)

*Primary Examiner* — Karen Cochrane Carlson
(74) *Attorney, Agent, or Firm* — Sughrue Mion, PLLC

(57) ABSTRACT

The present invention deals with examination of the alterability of part, or whole, of the surfaces of beta sheet-based protein structures, focusing especially on enzymes. The alteration is done by supplanting/transplanting a part, or whole, of the surface of one protein onto the surface of a homologous protein of superimposable polypeptide backbone, by exploiting the structural features of beta sheets to alter only the regions of the surface involved in substrate/ligand binding and catalysis. The transplantation involves replacement of a selected set of non-contiguous residues constituting the surface regions desired to be altered in one enzyme/protein, by a set of non-contiguous residues located at analogous positions in the other enzyme/protein, in a manner that is likely to facilitate folding and function of the new protein formed by combining residues from both enzymes/proteins. The present invention also deals with using this surface engineering approach to selectively combine enzyme/protein characteristics from different domains of life that are not ordinarily combined by natural evolution, such as the creation of novel proteins that retains the bulk of the thermostable scaffold of a thermophile enzyme onto which the active surface of a mesophile homolog is transplanted, so as to create a thermo-stable protein with meso-active functional characteristics of pH and temperature of optimal function.

5 Claims, 24 Drawing Sheets

(56) References Cited

OTHER PUBLICATIONS

Figure 1A:
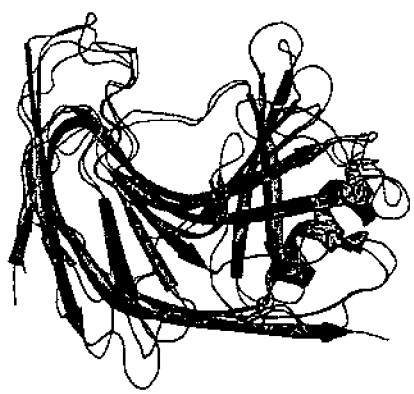

Arnott et al., "Thermostability and Thermoactivity of Citrate Synthesis from the Thermophilic and Hyperthermophilic Archae, Thermoplasma Acidophilum and Pyrococcus Furiosus," JMB, 2002, vol. 304: 567-668.

Ginalski et al., "Practical Lessons from Protein Structure Prediction," Nucleic Acids Research, 2005, vol. 33: 1874-1891.

* cited by examiner

FIG. 2A

```
1HOB  TVELCGRWDARDVAGGRYRVINNVWGAET---AQCIEVGL-ET-GNFTIT     46
MT    TVELCGQWDTRTVAGGRYTVSNNVWGAET---AQCIEVGL-ET-GNFTIT
1OA2  -ETSCDQWATFTGN--GYTVSNNLWGASAGSGFGCVTVVSLSGGASWHAD      47

D    N                    SN
1HOB  RAEHDN-GNLVAAYPAIYF----GCHWGACTNSSGLPRRVQELSDVRTSW     91
MT    RAEHDN-GNNVAAYPNIQPAIPQ--------------PRRVQELSDVRTSW
1OA2  -WQWSGGQNNVKSYQNSQTAIPQ--------------KRTVNSISSMPTTA    83

V    G
1HOB  TLTPIT-TGRWNAAYDIWFSPGTNSSNG---YSGGAELMIWLNWNGGVMP    137
MT    TLTPIT-TGRWNAAYDIPFAANPN---HVTYSGDAELMIWLNRNGDVMP
1OA2  SWSYSGSNIRANVAYDLPTAANPN---HVTYSGDYELMIWLGKYGDIGP    129

S
1HOB  GGSRVATVELAGATWEVWYADWD-WNYIAYRRTTPTTSVTELDLKAFIDD    186
MT    IGSRVATVELAGATWEVWYADNGAMNVISYVRTTPTTSVTELDLKAFIDD
1OA2  IGSSQGTVNVGGQSWTLYYGYNGAMQVYSFVAQTNTTNYS-GDVKNFFNY    178

1HOB  AVARGYIRP-EWYLHAVETGFELWEGGAGLRSADFSVTVQ              225
MT    AVARGYIRP-EWYLLSVQTGFELFTGGAGLRSADFSVTVQ
1OA2  LRDNKGYNAAGQYVLSYQFGTEPFTGSGTLNVASWTASIN              218
```

FIG. 2B

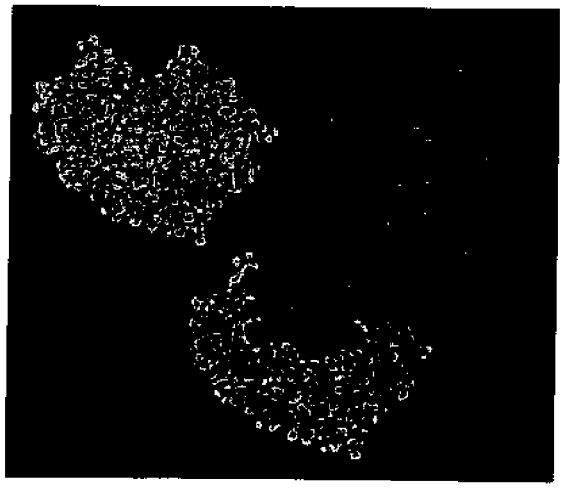

FIG. 11A

```
N-terminal Tag
              -12  M   R   G   S   H   H   H   H   H   H   G   S
               1   ATG AGA GGA TCG CAT CAC CAT CAC CAT CAC GGA TCC                    21
               1   ATG AGA GGA TCG CAT CAC CAT CAC CAT CAC GGA TCC                    20
              -12  M   R   G   S   H   H   H   H   H   H   G   S 2    T   V   E   L   C   R   G   W   D   A   R   D   V   H   G   R   Y   R   V
       ACT GTC GAG CTG TGT GGT AGA TGG GAC GCG CGC GAT GTG CAC GGG CGC TAC CGG GTG   41
       ACG GTC GAG CTG TGC GGA CAG TGG GAC ACG AGA ACG GTG CAC GGG CGC TAC ACG GTG   40
  1    T   V   E   L   C   G   Q   W   D   T   R   T   V   H   G   R   Y   T   V 22    I   N   V   W   G   A   E   T   A   Q   C   I   E   V   G   L   E   T   G
       ATC AAC GTA TGG GGT GCC GAG ACC GCA CAG TGC ATC GAG GTC GGG CTG GAG ACG GGC   61
       ATC AAC GTA TGG GGT GCG GAG ACC GCA CAG TGC ATC GAG GTC GGG CTG GAG ACG GGC   60
 21    I   N   V   W   G   A   E   T   A   Q   C   I   E   V   G   L   E   T   G 42    T   I   T   R   A   E   H   D   N   G   V   A   A   Y   P   A
       ACG ATC ACG CGG GCC GAG CAC GAC AAC GGC GTG GCC GCC TAT CCG GCC                77
       ACG ATC ACG CGG GCC GAG CAC GAC AAC GGC GTG GCC GCC TAT CCG AAC                67
 41    T   I   T   R   A   E   H   D   N   G   V   A   A   Y   P   N 62    I   Y   F   -   -   -   -   -   -   -   -   -   G   C   H   W   G   S   L
       ATC TAT TTC -   -   -   -   -   -   -   -   -   GGG TGC CAC TGG GGA TCG GGA TTG
       ATC CAG TTT GCC ATC CCG CAG -   -   -   -   -   -   -   -   -   -   -   -
 61    I   Q   F   A   I   P   Q   -   -   -   -   -   -   -   -   -   -   -   -
```

FIG. 11B

| | | | | | | | | | | | | | | | | | | | | |
|---|---|---|---|---|---|---|---|---|---|---|---|---|---|---|---|---|---|---|---|---|
| 78 | P CCG | R CGG | R CGC | V GTG | Q CAG | E GAA | L CTG | S TCC | D GAC | V GTG | R CGC | S AGC | W TGG | T ACG | L CTC | T ACG | P CCG | I ATC | T ACG | 97 |
| 68 | P CCG | R CGC | R CGT | V GTG | Q CAA | E GAA | L CTG | S TCC | D GAC | V GTG | R CGC | S AGC | W TGG | T ACG | L CTC | T ACG | P CCG | I ATC | T ACG | 87 |
| 98 | T ACA | G GGC | R CGC | W TGG | N AAT | A GCC | A GCC | Y TAC | D GAC | I ATC | W TGG | F TTC | S AGT | P CCC | T ACG | N AAT | — | — | — | 114 |
| 88 | T ACA | G GGG | R CGC | W TGG | N AAT | A GCC | A GCC | Y TAC | D GAC | I ATC | F TTC | F TTC | S GCC | P CCA | T AGC | — | — | — | — | 107 |
| 115 | S TCC | N AGC | — | — | Y TAC | G GGA | Y TAC | G GGC | A GCC | E GAG | L CTG | M ATG | I ATC | W TGG | L CTG | N AAC | N AAC | H CAC | — | 134 |
| 108 | — | — | — | — | Y TAT | S TCT | — | D GAC | A GCC | E GAG | L CTG | M ATG | I ATC | W TGG | L CTG | N AAC | K AAA | N AAC | — | 123 |
| 135 | V GTG | M ATG | P CCG | G GGT | G GGC | R CGC | V GTG | A GCC | E GAG | V GTG | L CTG | A GCC | W TGG | T ACC | T ACC | W TGG | E GAA | V GTC | G GGC | 154 |
| 124 | V GTG | M ATG | P CCT | I ATC | G GGC | R CGC | V GTG | A GCC | A GCC | V GTG | L CTG | A GCC | W TGG | T ACC | T ACC | W TGG | E GAA | V GTC | G GAT | 143 |
| 155 | W TGG | Y TAT | A GCC | D GAC | W TGG | Y TAC | I ATC | A GCC | Y TAC | R CGG | V GTG | R CGT | T ACG | P CCC | T ACC | T ACT | 173 |
| 144 | W TGG | Y TAT | A GCT | D GAC | W TGG | N AAT | M ATG | N AAT | V GTG | I ATC | S AGC | Y TAC | R AGG | V GTG | R AGG | T ACG | P CCC | T ACC | T ACT | 163 |

FIG. 11C

```
174 S   V   T   E   L   D   L   K   A   F   I   D   A   V   A   R   G   Y   I  193
    TCG GTG ACC GAA CTG GAC CTG AAG GCC TTC ATC GAC GCG GTC GCC CGC GGC TAC ATC
    TCG GTG ACC GAA CTG GAC CTG AAG GCC TTC ATC GAC GCG GTC GCC CGC GGC TAC ATC
164 S   V   T   E   L   D   L   K   A   F   I   D   A   V   A   R   G   Y   I  183

194 R   P   E   W   Y   L   H   A   V   E   T   G   F   E   V   A   R   G   A  213
    CGG CCG GAG TGG TAC CTG CAC GCG GTA GAG ACG GGC TTC GAA CTC TGG GAG GGG GCC
    CGG CCG GAG TGG TAC CTG CTG TCG GTA CAA ACG GGC GGC GAA CTC ACT GAG GGT GCC
184 R   P   E   W   Y   L   L   S   V   Q   T   G   G   E   L   T   E   G   A  203

214 G   L   R   S   A   D   F   S   V   T   V   Q                              225
    GGT CTG CGA AGC GCC GAT TTT TCC GTA ACG GTG CAG
    GGT CTG CGA AGC GCC GAT TTT TCC GTA ACT GTG CAG
204 G   L   R   S   A   D   F   S   V   T   V   Q                              215
```

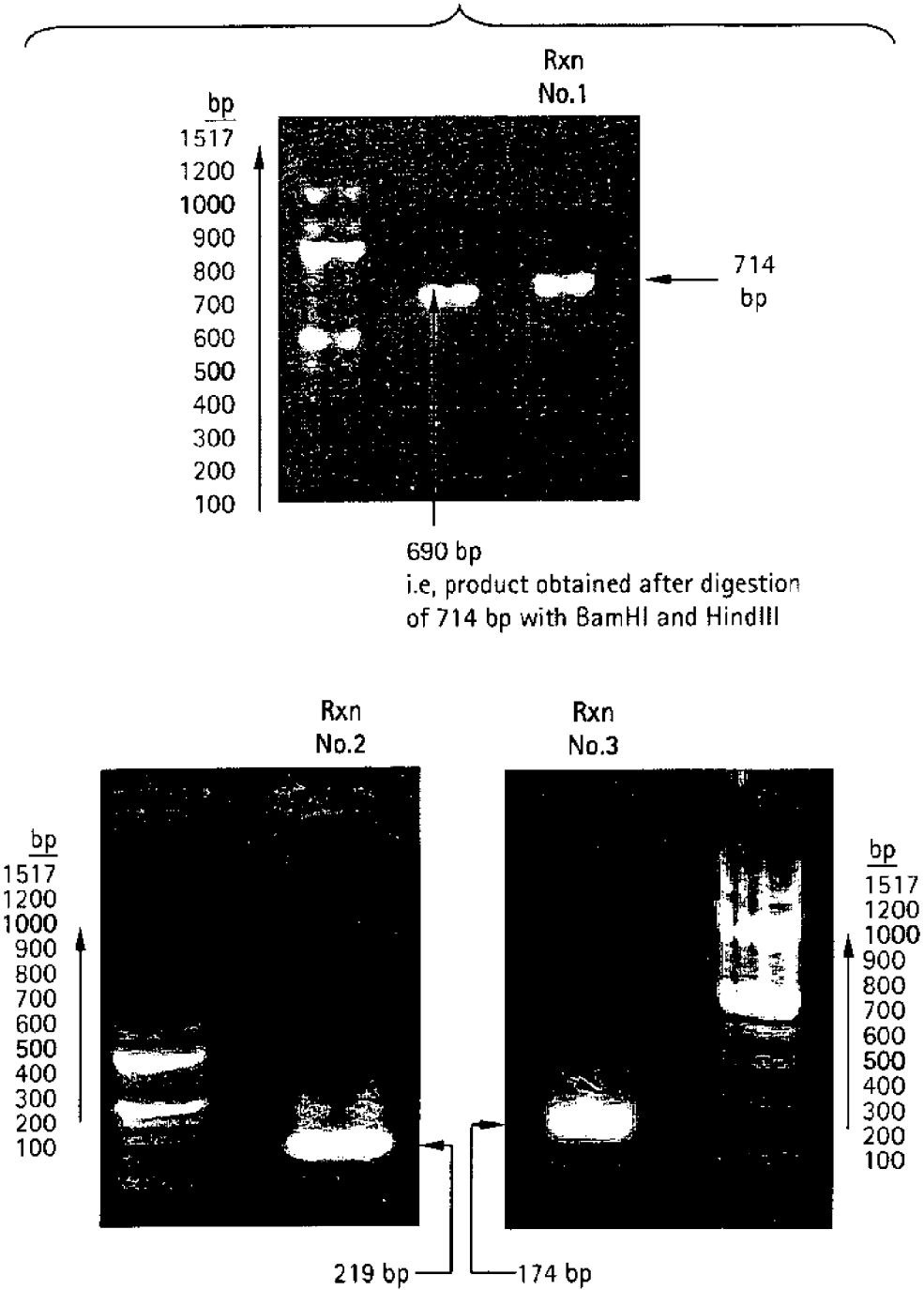

FIG. 13C
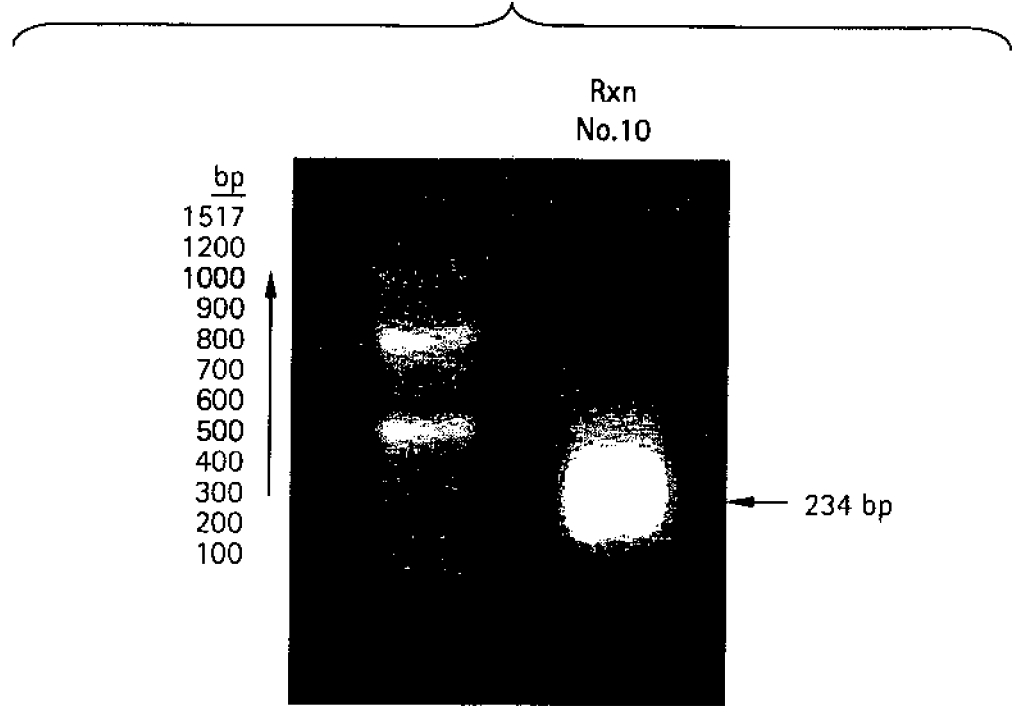
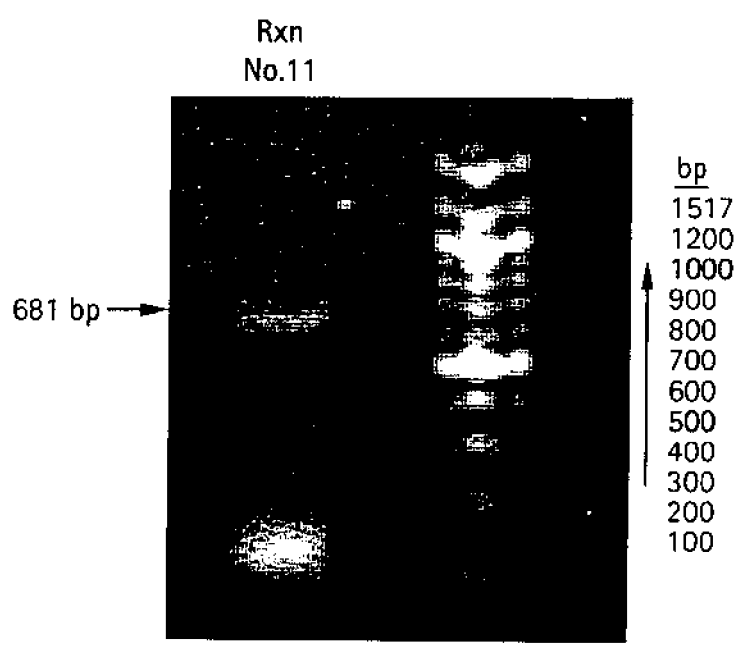

FIG. 14A

FIG. 16
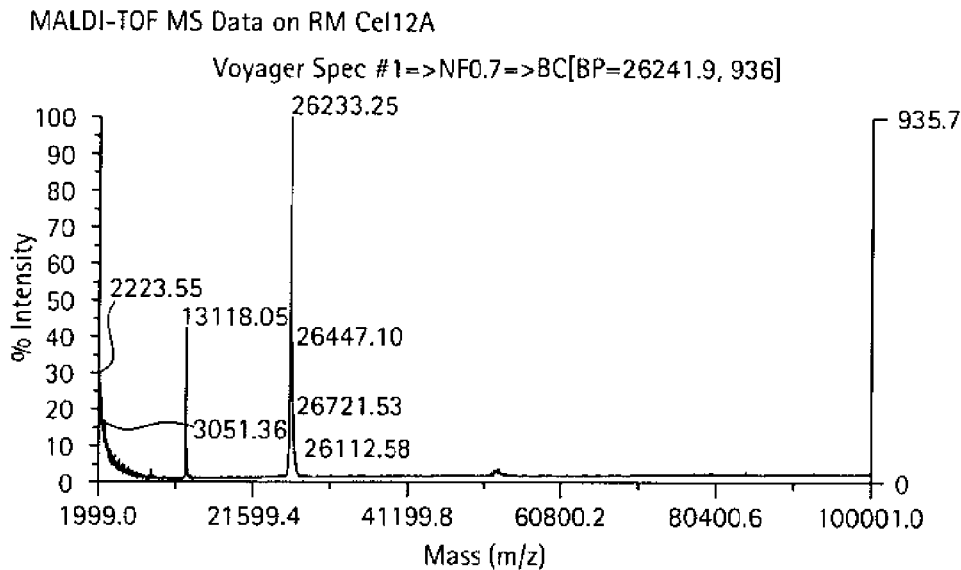
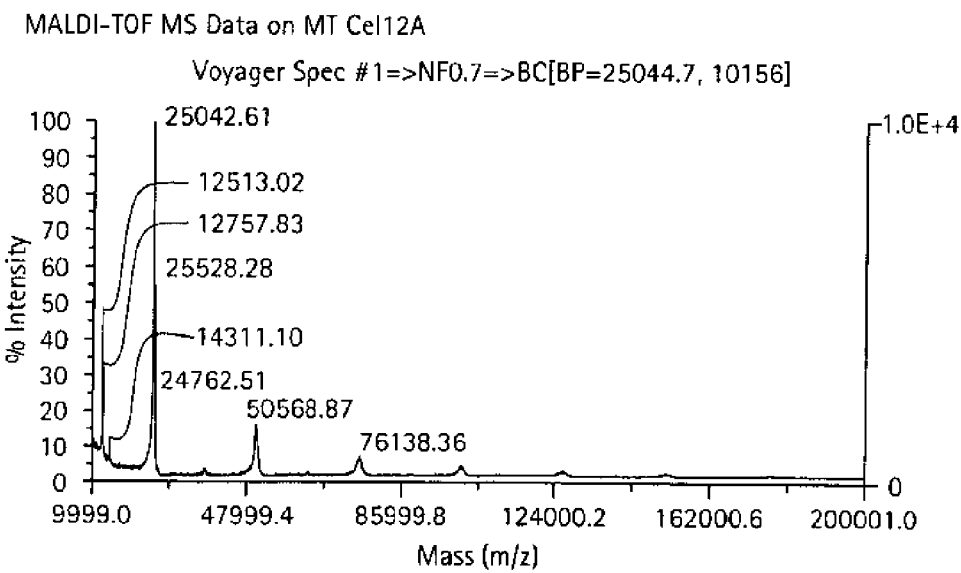

RECOMBINANT MESO-ACTIVE THERMO-STABLE PROTEIN AND PROCESSES OF DESIGN AND BIOSYNTHESIS THEREOF

This is a divisional of application Ser. No. 11/936,009 filed Nov. 6, 2007, which claims priority to Indian Patent Application No. 2411/DEL/2006, filed Nov. 6, 2006, the contents of all of which are incorporated herein by reference in their entirety.

FIELD OF THE INVENTION

The present invention provides a recombinant meso-active thermo-stable protein comprising the structural stability characteristics of a thermophile protein and the activity characteristics of a mesophile protein and its process of design and biosynthesis wherein a predominantly non-contiguous set of amino acids comprising the substrate-binding and catalytically active surface of the thermophile protein have been replaced by a different non-contiguous set of amino acids occurring at structurally equivalent positions in a structurally-homologous mesophile protein.

More particularly, it describes a generally-applicable approach for the deliberate alteration of the functional behavior of a protein molecule through rational residue replacement-based alteration, or 'notional transplantation', of a part (or parts) of its surface, by a set of residues comprising a functionally equivalent surface (or surfaces) within a different, independently evolved, structurally homologous protein possessing distinctly different characteristics in respect of structural stability, and physical activity, but the same chemical characteristics. The rational replacements of many different non-contiguously placed residues in the protein being altered, by residues used at equivalent locations in a homologous protein, lead by design to the folding of the altered protein into a three-dimensional structure imbued with the original structural stability characteristics of the unaltered form of the same protein, but the activity characteristics (e.g., the temperature of optimal activity) of the other (homologous) protein. This facilitates the creation of enzymes combining desired characteristics of enzymes sourced from different life forms, and different domains of life.

PRIOR ART AND BACKGROUND OF THE INVENTION

Protein Sequence-Structure Relationships: Common Wisdom:

A protein is a natural polymer of amino acids joined together by peptide bonds, which folds upon synthesis into a three-dimensional structure possessing some biological activity. The three dimensional structure of a protein is dictated by its amino acid sequence (Anfinsen, 1973. *Science* 181, 223). The amino acid sequence contains all the relevant information needed to dictate the formation of three-dimensional structure by a protein chain. Changes in a protein's sequence, effected through natural introduction of mutations during evolution, or by genetic engineering techniques, result in changes in the protein's structure. Such changes may be subtle, or profound. If the changes are subtle, they generally involve only minor alterations in the microstructure of a particular region of the protein, manifesting as changes in the shape of a local cluster of residues (either buried within the protein, or located on its surface) in the neighborhood of the altered residue, without any profound or visible effect on either the protein's overall shape or function, or the trajectory that its peptide backbone takes through its three-dimensional structure. When the changes are profound, however, they alter the entire shape of the protein as well as the trajectory that the backbone takes through the protein's structure. Sometimes, profound changes effected by mutations can even cause the chain to lose the ability to fold stably into a particular three-dimensional structure (resulting in aggregation, and precipitation). The effect of mutations on a protein's structure cannot always be correlated with, or calibrated to, the changes made in its sequence. Although the effects of very limited changes can nowadays be modeled computationally, experimental exploration of the effects of sequence changes becomes essential in all instances (regardless of whether these changes are subtle or profound), since all parameters, as well as physical forces, involved in determining the effects of these changes cannot yet be modeled. What is known very well today is that both profound and subtle alterations of sequence can lead to either profound, or subtle, alterations of structure in ways that defy predictability.

Thus, two proteins from two different organisms that are not evolutionarily related can sometimes be seen to have polypeptide backbones (although not amino acid residue sidechains) that are almost identical in their overall shape and folded structure, even though the two proteins have totally different amino acid sequences, with no similarity. However, this is more by way of exception, than the rule: generally, similarly sized proteins only tend to adopt substantially similar backbone structures if they have amino acid sequences that are somewhat similar (involving identity of at least as 20% of all residues). The outer shape characteristics of such proteins, however, are quite different, and this is on account of the specific 'decoration' of the backbone of each protein by specific groups of interacting residues (side-chains) peculiar to that protein, in a manner determined by its specific amino acid sequence. Conservation of backbone structure thus correlates with broad conservation of function; the precise thermodynamic and kinetic parameters of functionality are influenced almost entirely by the outer shape characteristics of the protein, which are determined by side-chains present on the protein's surface.

To summarize the above discussion, the precise relationship between amino acid sequence and protein structure is very subtle; all aspects of this relationship are not yet understood, or appreciated, and it is not yet possible to predict the effects of making particular changes in sequence on a protein's structure without doing the necessary experimentation, or without reference to a specific structural context. In this regard, and in specific relation to the reengineering of the surface of any protein through sequence changes, considerations of folding and stability play a role inasmuch as the engineering of the whole or part of a protein's surface affects its structure-forming ability, and its structural stability. Generally, in all efforts to engineer proteins, whether in regard to their surfaces or their interiors, two different approaches may be taken, these being: (i) a rational engineering approach based on structure-function analysis, and the deliberate introduction of specific mutations, and (ii) a non-rational (combinatorics-based and directed evolution-based) approach which relies more on random processes such as gene shuffling, or screening of phages displaying randomly generated populations of variants, followed by selection based on a binding trait. Within the field of protein engineering, the rational approach was the first approach adopted. However, because of the unpredictability of the effects of changes made, it proved to be less than satisfactory. Subsequently, newly available recombinant DNA techniques made combinatorics-based (combinatorial) approaches also feasible. The less-than-satisfactory results of the rational approaches led initially to a switchover to combinatorial approaches. Eventually, however, the infeasibility of exploring even a significantly small fraction of the sequence changes that can conceivably be made through an entirely random approach ($20^n$ changes for a chain of n residues) led to the adoption of hybrid approaches attempting to combine the best of both approaches. These hybrid approaches involve a rational selection of the residues or structural sites within proteins that are to be subjected to changes, and a non-rational (combinatorial search-based) exploration of the effects of making mutations at such sites.

Instances of Pure Rational Protein Engineering:

Rutter and coworkers introduced site-specific mutations at two positions in the active site of trypsin (following structural analysis of its active site) to reduce the catalytic rate but enhance the substrate specificity of the enzyme towards its natural substrate (Craik et al., 1985. *Science* 228, 291-297). Numerous other groups have subsequently introduced limited mutations, based on rational analysis of protein structures, to create variants with altered rate and/or affinity characteristics. Estell and coworkers engineered another protease, subtilisin, in respect of the electrostatics of the neighborhood of the enzyme's active site, to alter the preference for binding of substrates differing in their electrostatic characteristics (Wells et al., 1987, *Proc. Natl. Acad. Sci. USA* 84, 1219-1223). Perham and coworkers made rational mutations in glutathione reductase to leave its substrate specificity unaltered while changing its coenzyme specificity from $NADP^+$ to $NAD^+$ (Scrutton et al., 1990. *Nature* 343, 38-43). Several instances of such work followed during the decade of the nineties, in all of which limited rationally-selected mutations were introduced to alter enzyme characteristics in respect of the protein-ligand interactions in the proximity of the active site. Subsequently, bolder engineering attempts have been made which are described below. Benkovic and coworkers successfully designed a scytalone dehydratase-like enzyme using a structurally homologous protein scaffold of nuclear transport factor 2, demonstrating the efficacy of the rational engineering approach in developing new entities, by redesigning major sections of the scaffold protein (Nixon et al., 1999, *Proct Natl Acad Sci.* 96, 3568-3571). Similarly, Hellinga and coworkers analyzed the structure of a ribose-binding protein, rationally selected sites for 18-22 site-directed mutations that could be expected to impart triosephosphate isomerase (TIM) activity to this protein, and demonstrated this to be the case experimentally (Dwyer et al., 2004, *Science* 304, 1967-1971). Subsequently, combinatorial approaches also achieved success.

Instances of Pure Non-Rational (Combinatorial) Protein Engineering:

Directed evolution consists of the low frequency introduction of randomly distributed mutations in a gene of interest, followed by selection of the mutated (variant) proteins possessing the desired properties (Roberto et al., 2005, *Current Opinion in biotechnology.* 16, 378-384). Directed evolution has proven to be a powerful tool for the modification of proteins and has now become a widely used approach. It has been used mainly, however, in searching for temperature-sensitive and such-like mutants, using error-prone PCR to introduce mutations randomly into protein sequences, and in evolving novel binding reagents (through phage-display combinatorial approaches involving sections of proteins randomized by degenerate oligonucleotide incorporation into encoding DNA). There are very few instances of purely non-rational approaches having been used to alter enzyme activity, presumably because the mechanisms used to introduce mutations randomly cannot usually be controlled and restricted to a particular region of a protein's surface without some rational selection of sites, because the full exploration of the combinatorial space is impossible (there are too many variants that can be generated). With the human estrogen receptor alpha ligand binding domain, Zhao and coworkers used random mutagenesis and in vitro directed evolution to evolve a novel corticosterone activity (Chen et al., 2005, *J. Mol. Biol.* 348, 1273-1282).

Another notable example of the use of a purely random engineering approach (based, however, on a semi-rational selection of sites for randomization) was that of Bryan and coworkers who used directed coevolution to alter the stability and catalytic activity of calcium-free subtilisin (Strausberg et al., 2005, *Biochemistry* 44, 3272-3279). One example of the use of directed evolution to profoundly alter thermostability, but not activity, is that of Rao and coworkers who used this approach to develop a highly stable lipase (Acharya et al., 2004, *J. Mol. Biol.* 341, 1271-1281). By and large, the trend nowadays is to mix the rational and non-rational approaches, a few instances of which are cited below.

Instances of Hybrid (Rational-Combinatorial) Protein Engineering:

Some groups have used a hybrid approach which combines rational and combinatorial components to successful ends, as exemplified by the evolution of a new catalytic activity (β-lactamase activity) on the αβ/βα metallohydrolase scaffold of glyoxalase II by Kim and coworkers (Park et al., 2006, *Science.* 311, 535-538). A second example of the success of this approach is that of Peimbert and Segovia who have evolved a beta lactamase activity on a D-Ala D-Ala transpeptidase fold (Peimbert and Segovia, 2003, *Protein Engg.* 16, 27-35). Yet another example is the use of this approach to alter the specificity of the NHR human estrogen receptor in favor of a synthetic ligand, 4,4'-dihydroxybenzil, relative to the natural ligand, 17 beta-estradiol (Chockalingam et al., 2005, *Proc. Natl. Acad. Sci. USA* 102, 5691-5696).

Instances of Protein Structural Stability Engineering Through Modifications of Salt Bridges or Disulfides:

In addition, although this aspect has not been dealt with in detail, it may be noted that protein engineering involving rational approaches has also been attempted to achieve structural stabilization of specific proteins through the introduction e.g., of specific electrostatic interactions, or other additional bonds such as disulfide bonds. Such attempts have been based on the knowledge that surface salt bridges (Anderson et al., 1990. *Biochemistry* 29, 2403-2408) as well as disulfide bonds (Creighton, 1986, *Methods. Enzymol.* 131, 83-106) provide additional stability to proteins. However, such rational attempts have met with little success as exemplified by the work of Perham and coworkers (Scrutton et al., 1988, *FEBS Letters* 241, 46-50) who introduced a disulfide bond into glutathione reductase by design, to try and improve its stability, and produced an active enzyme that formed the intended disulfide bond but showed no additional structural stability.

The only previous instances we have been able to find of protein constructs attempting to somehow combine the structural stability of one protein with the temperature regime of activity of another (related) protein have involved trial-and-error approaches in which whole domains composed of contiguous stretches of residues, sourced from two different homologous proteins, have been recombined to generate chimeric proteins. We have been able to find four instances of the making of such chimeric proteins, two involving beta glucosidases from the work of Hayashi and coworkers (Singh and Hayashi, 1995, *J. Biol. Chem.* 270, 21928-21933; Goyal et al., 2001. *J. Mol. Catalysis. B: Enzymatic* 16, 43-51), one involving citrate synthase from the work of Danson and coworkers (Arnott et al., 2000, *J. Mol. Biol.* 304, 657-668) and one involving avidin (Hytonen et al., 2007, U.S. Pat. No. 7,268,216). In the first instance, chimeras of homologous β-glucosidases from *Agrobacterium tumefaciens* and *Cellvibrio gilvus* (~37% sequence identity; 40% sequence similarity) were made (Singh et al., 1995, op. cit.). In the second instance, chimeras of homologous β-glucosidases from *Agrobacterium tumefaciens* and *Thermotoga maritima* were made (Goyal et al., 2001, op. cit.). In the third instance, chimeras of homologous citrate synthases from *Thermoplasma acidophilum* and *Pyrococcus furiosus* were made (Arnott et al., 2000, op. cit.). In all three instances, the intention was to obtain chimeras with enzymatic properties of improved enzymatic stability and altered temperature and pH of optimal function. In a fourth instance, which was found in the patent literature (Hytonen et al., 2007. op. cit.), the thermal stability of a chicken avidin protein was improved by replacing one of its structural domains, named beta 4, with the entire beta 4 domain of a different avidin-related (AVR) protein.

Disclosure of the Present Invention, Novelty of the Present Invention, and Differences Between the 'Chimera' Approach and the Approach Proposed in the Present Invention We have explored, in this invention, the micro-structural and macro-structural effects of sequence alterations on protein surfaces (drawn from evolutionary comparisons of proteins), with particular reference to using such alterations to create, by design (rather than through non-rational combinatorial approaches) novel proteins that combine the structural features of one protein with the functional features of another (homologous) protein sourced from a different organism. Therefore, in this invention, our emphasis is on protein surface reengineering, with specific reference to engineering of the physical parameters circumscribing protein enzymatic activity and/or other function (e.g., protein-protein interactions).

DISCLOSURE OF THE PRESENT INVENTION

We superimposed the structures of two beta sheet-based beta jelly-roll fold proteins, RM Cel12A (SEQ ID NO:1) and TR Cel12A (SEQ ID NO:2), which are cellulose-degrading enzymes known as cellulases. We confirmed that the polypeptide backbone atoms of the two enzymes are superimposable to a root mean square deviation of 1.1 Angstroms. We then created corresponding sets of about 60 analogous residues in both enzymes that comprise their active surfaces. The active surfaces here are defined as the entire solvent-exposed surfaces of the twisted/curved, structurally-homologous, beta sheets in the two enzymes that contain the substrate(cellulose)-binding grooves. Considering SEQ ID NO:1 to be the host enzyme, and retaining most of its amino acid sequence, we then incorporated mutations in this sequence at positions locating on the active surface of the folded enzyme structure, so as to replace all such residues by those used at the structurally-analogous positions in the other (guest) enzyme structure, which has the amino acid sequence represented by SEQ ID NO:2. The purpose of this replacement was to replace the entire set of 60 predominantly non-contiguous residues (drawn from all over the polypeptide chains of the host enzyme) that constitute its active surface, by the structurally-equivalent residues constituting the active surface of the guest enzyme. This replacement leads to the formation of a mutated form of the host enzyme represented by SEQ ID NO:3. It effects a mimicking of the active surface of the guest enzyme on the folded structure of the mutated form of the host enzyme, such that SEQ ID NO:3 folds to display the structural stability characteristics of RM Cel12A and the activity characteristics of TR Cel12A. As RM Cel12A is a thermophile cellulase, and TR Cel12A is a mesophile cellulase, we refer to the mutated form of RM Cel12A (incorporating the active surface of TR Cel12A) as a meso-active thermostable cellulase, MT Cel12A. MT Cel12A has been characterized both structurally and functionally, using X-ray crystallography, circular dichroism spectroscopy, mass spectrometry, gel filtration chromatography and gel electrophoresis, and cellulase activity assays. It was demonstrated that MT Cel12A is truly a meso-active thermo-stable enzyme combining the active surface of TR Cel12A and the bulk of the structural stability characteristics of RM Cel12A.

Novelty of the Approach Proposed in this Invention

In summary, all of the successful uses of engineering approaches described above, in the prior art and background, relate to attempts to use protein engineering (employing either rational or combinatorial approaches) to alter either: (a) the chemical specificity of protein/enzyme active sites in respect of the preference for binding of substrate, or other ligand (e.g., coenzyme), or (b) the thermodynamic and kinetic parameters of binding of a substrate, or ligand. In contrast, in this invention, we propose to alter protein/enzyme surfaces in respect of the physical characteristics (i.e., the temperature of optimal binding, or activity) of enzyme/protein function, rather than the chemical characteristics of function relating, e.g., to the preferential binding of a substrate, or ligand, of a particular chemical structure. We propose to employ a rational engineering approach rather than a combinatorial, or hybrid, approach, but one that is systematic enough to have a high probability of working for all proteins in which the functional part of the protein (i.e., its active surface, or active domain, or sub-domain) is dominated by a particular type of secondary structure, the beta sheet structure. Introducing mutations in β-sheets (on an entire solvent-facing side of the sheet) is much easier done without perturbing the sheet than introducing mutations in α-helices that are on a protein's surface, because in β-sheets alternate residues face away in opposite directions, and 'next-neighbor' residues do not interact with, or interfere with, each other. In α-helices, on the other hand, 'next-neighbor' residues being present on the same side, or face, of the helix, greatly influence each other, because of which even a single mutation performed without making accompanying (compensating) mutations in the immediately neighboring residues can greatly upset structure-formation and stability. Our case is that the unpredictability of the effects of mutations apply much more to helical than to sheet structures. We propose to make mutations on beta sheet surfaces designed rationally using a detailed understanding about the structure/function relationships of all-beta structures, to explore how far rational approaches may be taken. It may be noted that there are no examples of this in the art to our knowledge, thus none are being cited here.

Differences Between the 'Chimera' Approach and the Present Invention

As stated already, one of our objectives is to create novel proteins/enzymes bearing the structural stability characteristics of a thermophile (thermostable) analog, and the functional characteristics of a mesophile analog acting on the same substrate. Also, as already stated (in the prior art and background), the only class of previous efforts in this direction (i.e., with similar overall objectives) involve the swapping of whole domains comprising contiguous stretches of residues, to generate chimeric proteins. In chimeric proteins, there is no remodeling of protein surfaces at the level of any individual secondary structural, or super-secondary structural element (such as a beta sheet), but rather a mixing of fully autonomously-folded domains from two different multi-domain proteins performing similar functions. In proteins, in general, it is well known that the level of interactions amongst domains is always far lower (in terms of the number of residue-residue contacts involved) than the level of interactions amongst structural elements within domains, or of interactions amongst residues within a single secondary or supersecondary structural element. Indeed, often two autonomously folded domains do not even directly interact from a structural viewpoint, whereas residues within secondary and supersecondary structural elements within domains engage in extensive and intimate interactions. As a consequence, it is generally a simple and trivial task to combine domains from different proteins into the same polypeptide chain and manage to retain function in both domains, because concerns regarding domain-domain interactions are far fewer.

Such simple (chimera-type) combinations of contiguous stretches of sequence cannot be successfully performed to remodel a single-domain protein, because in such chimeras sequences drawn from the two proteins would be located both on the surface and in the interiors. Residues from secondary structural elements preevolved in two different proteins cannot be forced to meet and bind to each other at the interface of two structures within the interior of any protein, because the formation of an interface would require a high degree of shape complementary and chemical compatibility. Simple chimeras cannot avoid such conflicts of shape complementarity and chemical incompatibility at structure-structure interfaces in their interiors. Presumably as a consequence of this, there is no known successful instance of the construction of any chimera involving a single domain protein in which a contiguous stretch of amino acids has been supplanted by an equivalent stretch from another protein.

Our invention avoids the above-mentioned problems, and successfully combines characteristics of two single domain proteins, by engineering only surface residues, and only within beta sheet-based structures. Our approach works for the following reasons: (i) Surface residues lying adjacent to each other only need to interact with the solvent and with each other within a defined region of a protein's surface in which all residues are drawn from the same protein, and thus have a pre-evolved scheme of engaging in interactions to create the surface. Unlike in chimeras, these residues do not have to interface with another set of residues drawn from a different protein with a buried interior location, thus obviating problems of shape complementarity and chemical incompatibility. (ii) We use the entire surface of a structural element (a secondary or supersecondary structural element) such as, e.g., the entire solvent-exposed face of a beta sheet, and not a part of the surface of any structural element. This obviates shape complementarity and chemical compatibility problems within the surface of the structural element, and restricts such problems only to the edges of the surface where it meets another part of the surface of a different structural element where, in any case, because of solvent exposure there exists a greater degree of flexibility and adaptability.

Therefore, in summary, the chimera approach cited in the prior art differs from the approach proposed in this invention in the following respects:

Their choice of similar enzymes was based on sequence similarity amongst enzymes of known sequence. In contrast, our choice is based on structural (backbone) superimposability amongst enzymes of known structure.

Their attempt to improve, the stability, temperature optima and pH optima was based on the assumption that these characteristics lie vested within individual domains defined by contiguous stretches of sequence within the overall sequence, without evidence being provided to support the assumption that such characteristics are indeed defined by separate domain-like structures. In contrast, our approach does not ascribe properties to contiguous stretches of residues. Rather, we hold the optimal pH and temperature characteristics to be a function of the interactions and flexibilities of the solvent-exposed residues constituting the active surface alone (a decidedly non-contiguous set of residues brought together in three-dimensions by chain folding). We hold structural stability to be largely a function of buried residues constituting the hydrophobic core of a protein. Therefore, the construction of our novel protein involves mutations of non-contiguous residues that lie together in the structure (and not in the sequence). We make mutations that transplant only the active surface of a thermostable enzyme by the active surface of a homologous mesophile enzyme, based on structural principles and understanding that are being elucidated for the first time in the literature.

As a result of the basic differences in approach detailed above, Hayashi and coworkers (Singh and Hayashi, 1995, *J. Biol. Chem.* 270, 21928-21933; Goyal et al., 2001, *J. Mol. Catalysis. B: Enzymatic* 16, 43-51) as well as Danson and coworkers (Arnott et al., 2000, *J. Mol. Biol.* 304, 657-668) have managed to only create chimeras with stability and functional characteristics that are either intermediate to those of the two enzymes from which sequences were derived to make the chimera, or altogether different from the two parent sequences, in entirely unpredictable ways. In contrast, our approach proposes to rationally and predictably mix the functional characteristics of one parent (i.e., the exact pH and temperature optima) with the stability characteristics of the other, to derive a protein that largely retains these features.

In the chimeras, there is no selection of residues from either progenitor enzyme based on the location of the residue in either the interior of the protein, or on the surface of the protein. This makes the approach useful only for simple mixing of domain-encoding sequences from multi-domain proteins. In contrast, our approach focuses on a structure-based selection of solvent-exposed residues

OBJECTIVES OF THE INVENTION

The objective of the present invention is to provide a recombinant meso-active thermo-stable protein comprising the structural stability characteristics of a thermophile protein and the activity characteristics of a mesophile protein and its process of synthesis wherein a predominantly non-contiguous set of amino acids have been replaced by a different non-contiguous set of amino acids occurring at structurally equivalent portions of a structurally-homologous protein.

Moreover, the invention provides a methodology for systematic alteration of the functional behaviour of any protein made up predominantly of beta structures.

Another object of the invention is to supplant/transplant the entire surface of one protein, or a part of the surface, onto the surface of a homologous protein with a high degree of superimposability of backbone.

Yet another object is to transplant an active surface from a mesophile onto a thermophile protein, to produce a recombinant thermostable protein.

Still another object is to produce a recombinant thermostable protein showing stability characteristics of a thermophile, and the activity profile of a mesophile protein, thus providing a methodology for combining structural and functional attributes not ordinarily combined through natural evolution.

SUMMARY OF THE INVENTION

The present invention deals with beta sheet-based protein structures, and focuses especially on enzymes, examining the alterability of protein surfaces. This is done by supplanting/transplanting the entire surface of one protein onto the surface of a homologous protein of overlapping backbone trajectory (i.e., whole surface transplantation) or only altering the regions of the surface involved in catalysis and/or substrate/ligand binding (i.e., active surface transplantation). The present invention also deal with selective mixing and matching of non-contiguous and/or contiguous residues, to achieve transplantation of surfaces including beta strands and/or intervening loops from beta sheet structures. The present invention also deals with performing surface engineering involving the transformation of a protein of thermophile functional characteristics into a protein of mesophile functional characteristics, while retaining the structural characteristics of the thermophile protein.

Accordingly, the present invention provides a recombinant meso-active thermo-stable protein comprising the structural stability characteristics of a thermophile protein and the activity characteristics of a mesophile protein.

In an embodiment of the present invention the recombinant meso-active thermo-stable protein comprises a protein with a single structural domain wherein a predominantly non-contiguous set of amino acids has been replaced by a different non-contiguous set of amino acids occurring at structurally equivalent portions of a structurally-homologous protein.

In an embodiment of the present invention a part OR the whole of the surface of a "guest" or "donor" progenitor protein is notionally transplanted onto the structural core of a "host" or "recipient" progenitor protein.

Yet, in another embodiment of the present invention the guest and host progenitor proteins have homologous structures and identical functions.

Yet, in another embodiment of the present invention the guest progenitor protein is a mesophile protein and the host progenitor protein is a thermophile protein.

In an embodiment of the present invention the functionally-active surface regions of the homologous guest and host progenitor proteins comprise beta sheet-based secondary structure.

In an embodiment of the present invention the thermophile host progenitor protein and mesophile guest progenitor used have the amino acid sequences represented by SEQ ID NO:1 and SEQ ID NO:2, respectively and the recombinant meso-active thermo-stable protein comprising the amino acid sequence represented by SEQ ID NO:3.

In another embodiment of the present invention the recombinant meso-active thermo-stable protein has the following characteristics:
1. molecular mass: 20-30 kiloDaltons;
2. number of residues: about 200-300;
3. isoelectric point: ranging between 4-8;
4. pH of optimal activity: ranging between 4-8;
5. temperature of melting ($T_m$): 80-95 degrees Centigrade, and
6. temperature of optimal activity ($T_{OA}$): ranging between 30-60 degrees Centigrade.

Yet in another embodiment of the present invention the said protein and its progenitors are enzymes of the structural class of single-domain beta sheet proteins belonging to the group of hydrolases and is selected from the group consisting of cellulase, xylanase, amylase and protease, preferably cellulase.

In yet another embodiment of the present invention the recombinant meso-active thermo-stable protein can also function as a biocatalyst.

In yet another embodiment of the present invention the process for the design of recombinant meso-active thermo-stable protein comprises the structural stability characteristics of a host progenitor protein and the activity characteristics of a different and structurally homologous guest progenitor protein.

In an embodiment of the present invention the structurally-homologous host and guest progenitor proteins comprises structures in which substrate-binding and catalytic functions are provided by residues located on a beta sheet-based secondary structure.

In an embodiment of the present invention the process for the design of recombinant meso-active thermo-stable protein; comprise the steps of:
a. superimposing the structures of the guest and host progenitor proteins and estimating the degree of superimposability of their structures at the level of the polypeptide backbone, preferably in the region of the structure comprising the substrate-binding and catalytic functions,
b. generating structural analogy-based sequence alignments of the protein sequences and the encoding DNA sequences of the host and guest progenitor proteins by using the information of step (a),
c. identifying the particular amino acid residues in the sequence of the host progenitor protein which constitute the beta sheet-based 'active surface' and using the aligned sequences obtained from step (b) to identify the corresponding analogous non-contiguous residues and groups of residues in the guest progenitor protein,
d. determining the particular residues that are identical in the two corresponding sets of amino acid residues from the host and guest progenitor proteins constituting the active surfaces of the two proteins and eliminating the identical residues to obtain a set of corresponding non-identical residues occurring at structurally-equivalent positions in the two proteins,
e. mutating the host progenitor protein at the positions in its beta sheet-based 'active surface' which are non-identical with the corresponding residues in the guest progenitor protein, f. replacing the residues present in the host progenitor protein with the residues present in the guest progenitor protein resulting in constituting the novel meso-active thermo-stable protein, g. biosynthesizing the novel meso-active thermo-stable protein by known recombinant DNA methods, followed by isolation and purification by known methods and h. confirming the structural stability characteristics of the host progenitor protein and the physical and chemical activity characteristics of the guest progenitor protein in the desired meso-active thermo-stable protein by activity measurements.

In an embodiment of the present invention the amino acid residues constituting the structural core of the product meso-active thermo-stable protein are derived from one of the two progenitor protein, while the residues constituting a part OR the whole of the surface of the product protein are derived from the other progenitor protein.

In an embodiment of the present invention, the two progenitor proteins are structurally homologous with the coordinates of their backbone atoms being superimposable to a root mean square deviation (RMSD) of 0.5-2.5 Angstroms.

In an embodiment of the present invention, the temperatures of optimal function and structural melting within the host and guest progenitor proteins used are within 5 degrees Centigrade apart, In another embodiment of the present invention, the structurally-homologous 'active surface' regions of the two progenitor proteins comprises primarily beta sheet-based secondary structure.

Yet, in another embodiment of the present invention the guest progenitor used is a thermophile protein RM Cel12A of SEQ ID NO:1 and the host progenitor used is a mesophile protein TR Cel12A of SEQ ID NO:2.

In an embodiment of the present invention the amino acid residues constituting the structural core of the product protein are derived from RM Cel12A, while the residues constituting a part of the surface of the product protein are derived from TR Cel12A.

In an embodiment of the present invention the RM Cel12A and TR Cel12A proteins are structurally homologous with the coordinates of their backbone atoms being superimposable to a root mean square deviation (RMSD) of 0.5-2.5 Angstroms.

In an embodiment of the present invention the temperatures of optimal function and structural melting within RM Cel12A and TR Cel12A are within 5 degrees Centigrade apart.

In an embodiment of the present invention the structurally-homologous 'active surface' regions of RM Cel12A and TR Cel12A comprise primarily beta sheet-based secondary structure.

In an embodiment of the present invention the product MT Cel12A of SEQ ID NO:3 is derived from the host progenitor by replacing the residues comprising the host progenitor's active surface by structurally-analogous residues comprising the guest progenitor's active surface.

In yet another embodiment of the present invention the novel meso-active thermo-stable (MT Cel2A) products obtained possesses the optimal temperature of activity of the mesophile guest progenitor, TR Cel12A, and the structural stability of the homologous thermophile host progenitor, RM Cel12A.

In yet another embodiment of the present invention the meso-active thermo-stable protein (MT Cel2A) has the following characteristics:
1. molecular mass: 20-30 kiloDaltons;
2. number of residues: about 200-300;
3. isoelectric point: ranging between 4-8;
4. pH of optimal activity: ranging between 4-8;
5. temperature of melting ($T_m$): 80-95 degrees Centigrade, and\
6. temperature of optimal activity ($T_{OA}$): ranging between 30-60 degrees Centigrade Yet, in another embodiment of the present invention the process is useful for modulating the physical functional characteristics of enzymes without altering the chemical characteristics of the enzyme activity or the chemical definition of the substrate.

Yet, in another embodiment of the present invention the process is useful for recombining enzyme structural stabilities with protein stability and activity characteristics from two very different domains of life.

In an embodiment of the present invention the meso-active thermo-stable protein is useful for applications in the textile industry such as stone-washing of denim fabrics.

BRIEF DESCRIPTION OF FIGURES AND TABLES

Figure 1B:
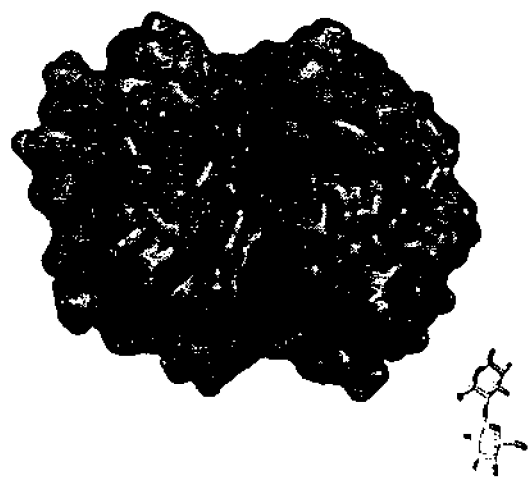
Figure 1C:
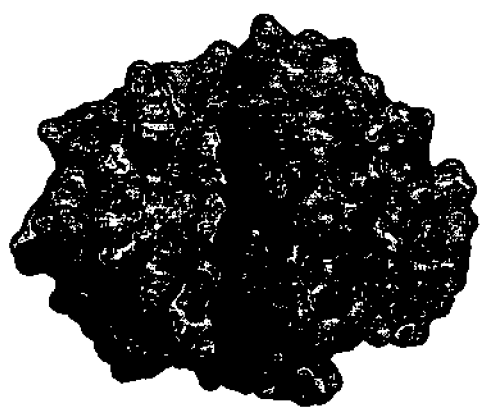

FIGS. 1A-1C: Structural similarities and dissimilarities between RM (red), and TR (blue) Cel12A. FIG. 1A shows polypeptide backbones superimposed with an RMSD of 1.1 Å. Note the sandwiched upper and lower sheets, and the concave groove created by the top sheet constituting the cellulose-binding 'active surface'. FIGS. 1B and 1C, respectively, show top-views of the TR Cel12A and RM Cel12A surfaces, highlighting the 19-21 Å long cellulose-binding grooves. Note dissimilarities of the microstructural features of the two grooves.

FIGS. 2A and 2B: Structure-based sequence alignment and surface representations of RM (red), TR (blue), and modeled MT (red-blue) Cel12. FIG. 2A. Green boxes highlight 'active surface' residues in RM Cel12A (1H0B) represented by SEQ ID NO:1, and TR Cel12A (1OA2) represented by SEQ ID NO:2, which are either conserved (three rows) or non-conserved (two rows). Single residues above top row indicate discrepancies between expected and obtained sequences, with the residue reported for 1HOB in the literature being shown above the residue obtained by us through sequencing of our clone (SEQ ID NO: 1). The sequence mentioned in the middle row is the sequence of MT Cel12A (SEQ ID NO:3). Note the clusters of alternating 'active surface' residues from beta strands. FIG. 2B. Side-views of surfaces of RM (red). TR (blue), and modeled MT (red-blue) Cel12A. The MT Cel12A model is color-coded to indicate differential sourcing of residues from RM and TR progenitors.

FIGS. 3A-3F: Quaternary and secondary structures of RM and MT Cel12A at pH 8.0 and pH 5.0. Superdex-75 chromatograms of elutions in the absence (black lines), and presence (red lines) of 100 mM NaCl are shown for MT Cel12A in FIG. 3A (pH 8.0) and FIG. 3B (pH 5.0), and for RM Cel12A in FIG. 3C (pH 8.0) and FIG. 3D (pH 5.0). Note elution of MT and RM Cel12A at 1.23 ml (monomer) in the absence of salt, and at later volumes in the presence of salt, and at low pH. Far-UV CD spectra of enzymes in the presence of 100 mM NaCl at pH 8.0 (black lines) and pH 5.0

Figure 3A:
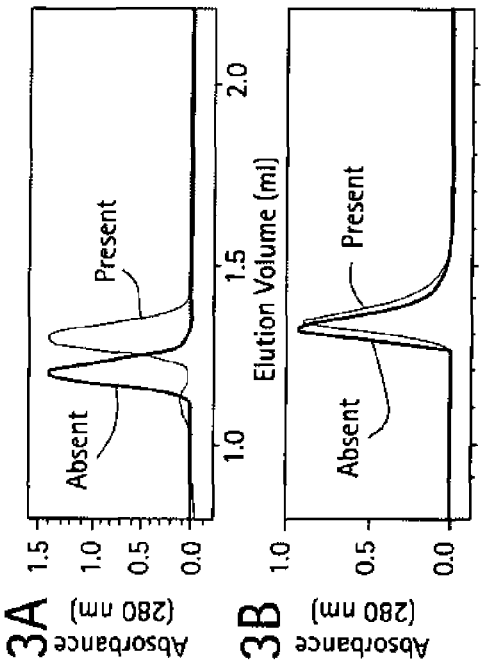
Figure 3B:
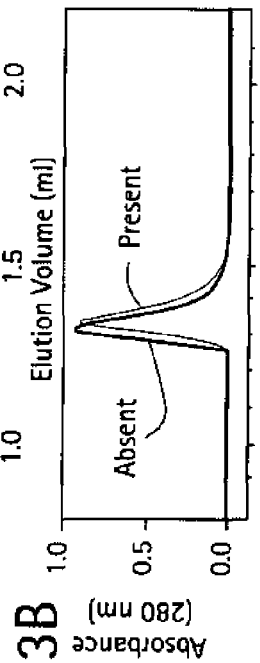
Figure 3C:
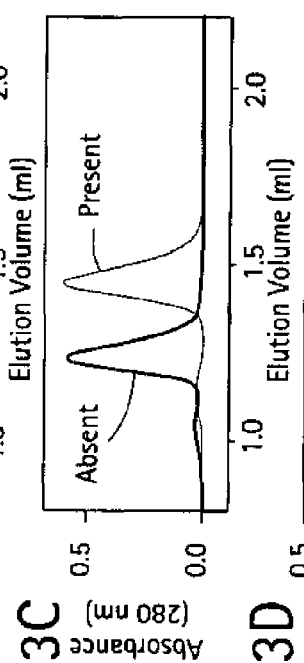
Figure 3D:
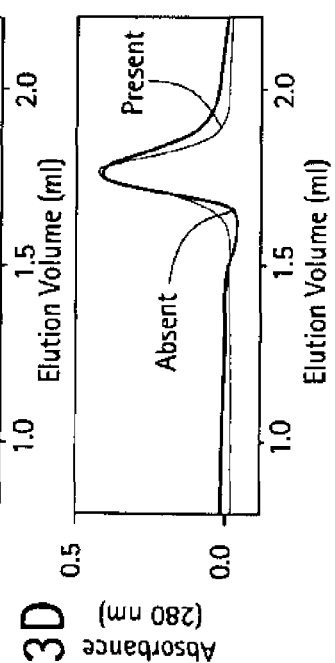
Figure 3E:
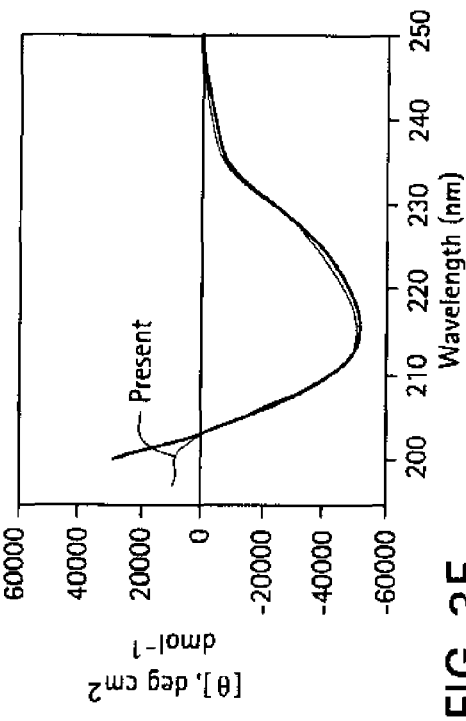
Figure 3F:
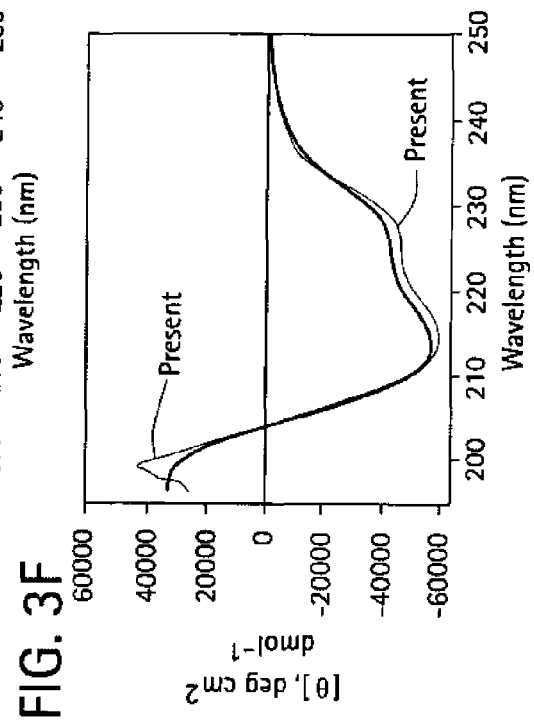

(red lines) are shown in FIG. 3E (MT Cel12A) and FIG. 3F (RM Cel12A). Identical spectra were obtained in the absence of salt (not shown).

Figure 4A:
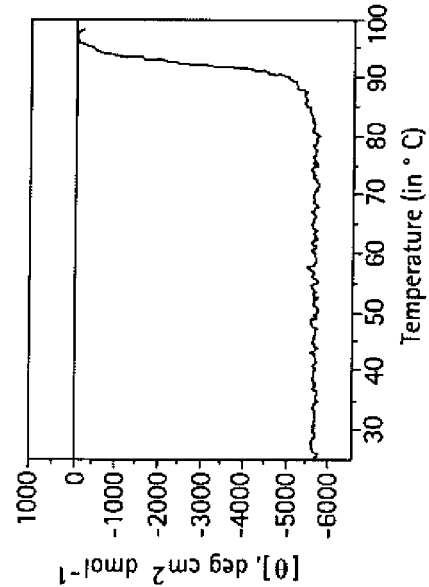
Figure 4C:
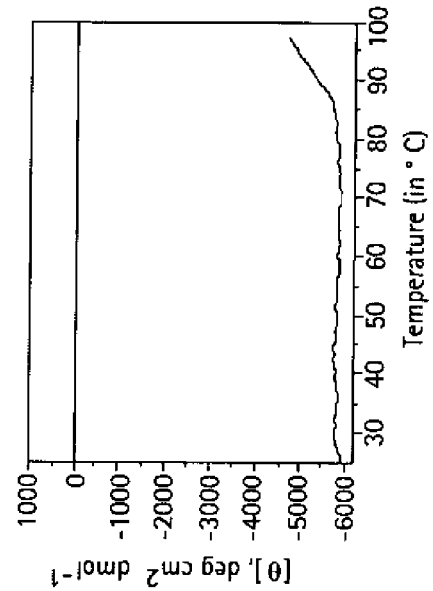
Figure 4B:
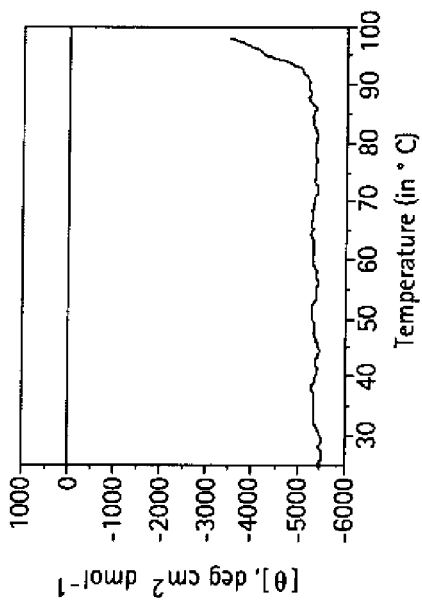
Figure 4D:
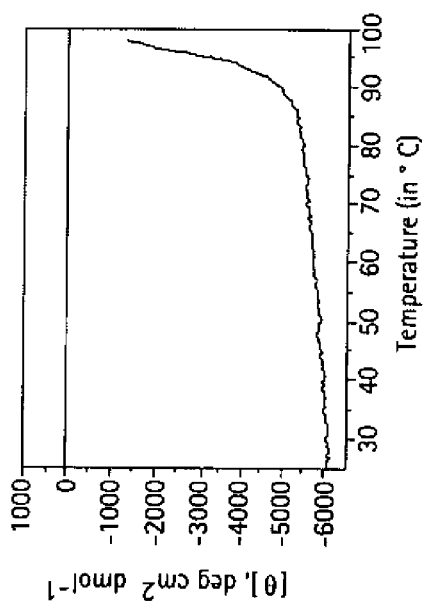

FIGS. 4A-4D: Thermal stability of RM and MT Cel12A at pH 8.0 and pH 5.0. Temperature-dependent changes in mean residue ellipticity at 218 nm are shown in FIG. 4A (RM Cel12A, pH 5.0). FIG. 4B (MT Cel12A, pH 5.0). FIG. 4C (RM Cel12A, pH 8.0) and FIG. 4D (MT Cel12A, pH 8.0). Note occurrence of structural changes only above 85° C. in all situations, and the RM Cel12A-like thermal stability of MT Cel12A at both pH 8.0 and pH 5.0.

Figure 5A:
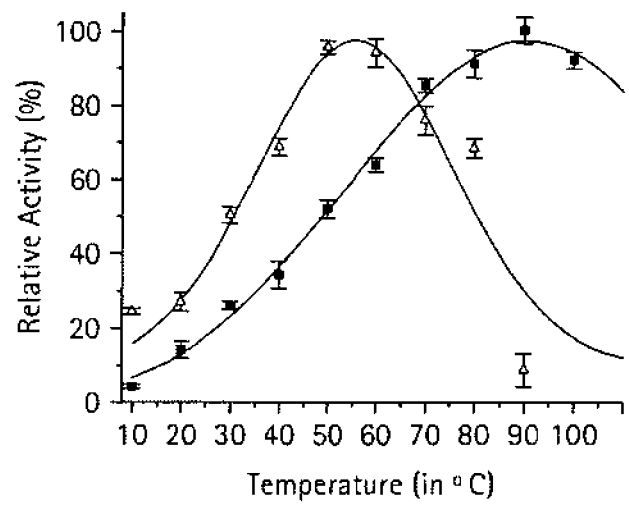
Figure 5B:
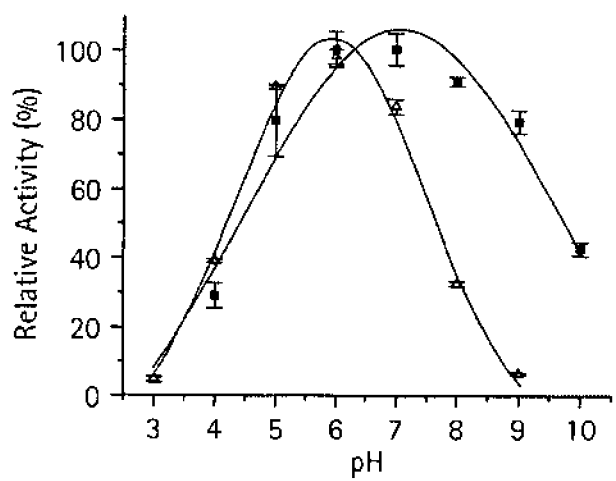

FIGS. 5A and 5B: Temperature- and pH-dependence of activity of MT and RM Cel12A. FIG. 5A: Variations in MT (open triangles) and RM (solid squares) Cel12A activities measured at pH 5.0 as a function of temperature. FIG. 5B: Variations in MT (open triangles) and RM (solid squares) Cel12A activities measured at 50° C. as a function of pH. Mean values and standard error bars are based on 5 experiments each. Note that MT Cel12A has temperature and pH optima close to that of TR Cel12A (this figure), even though it has a structural stability comparable to that of RM Cel12A (FIG. 4).

Figure 6:
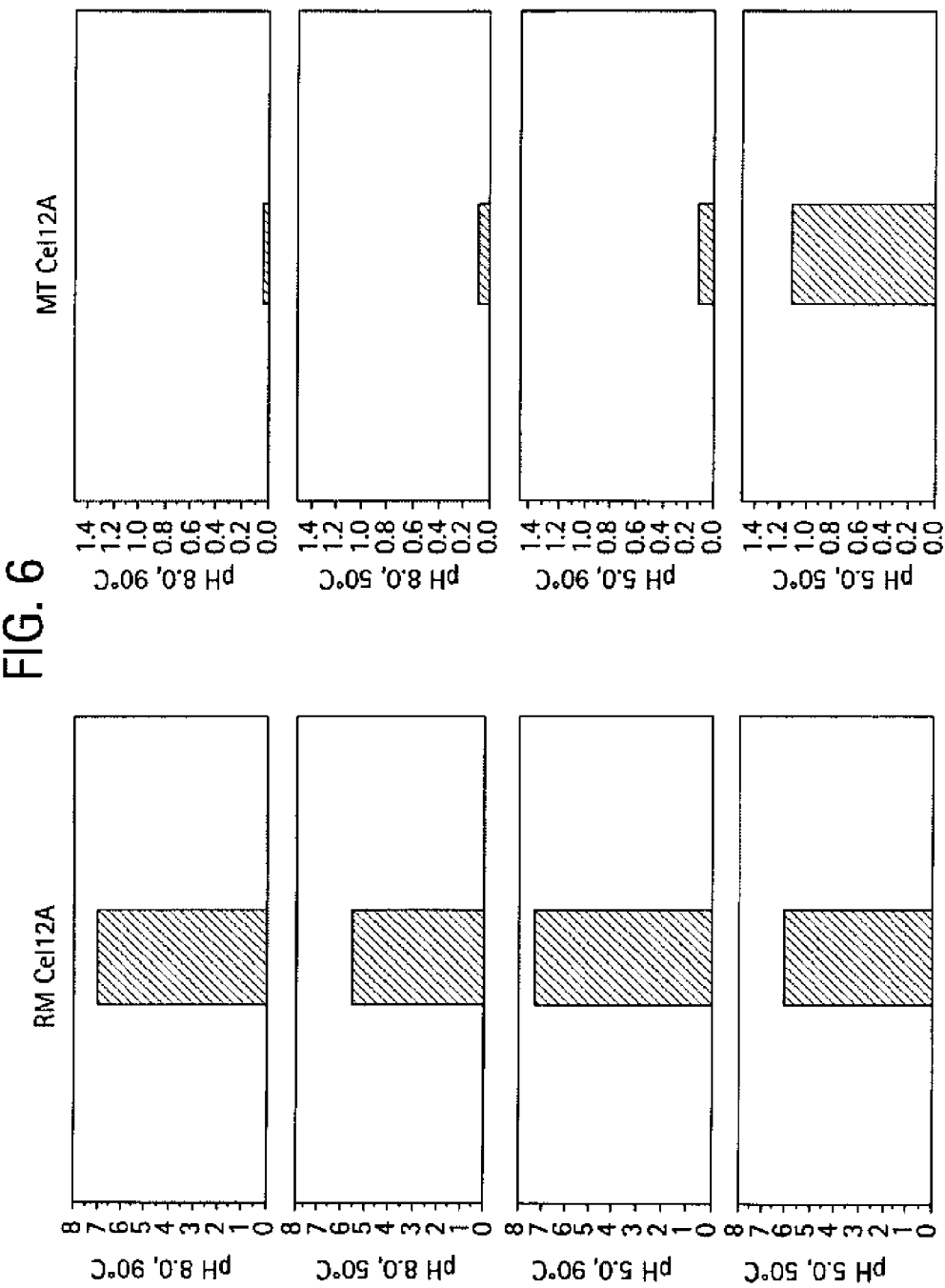

FIG. 6: Comparisons of RM Cel12A and MT Cel12A activities at various temperatures and pH values. The ordinates show optical densities at 550 nm for DNSA-reacted reducing sugars. The scales for the RM Cel12A data (0 to 8) are shown differently from those for MT Cel12A (0 to 1.5) to allow better visual comparison.

Figure 7A:
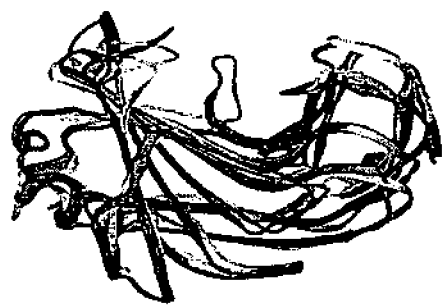
Figure 7B:
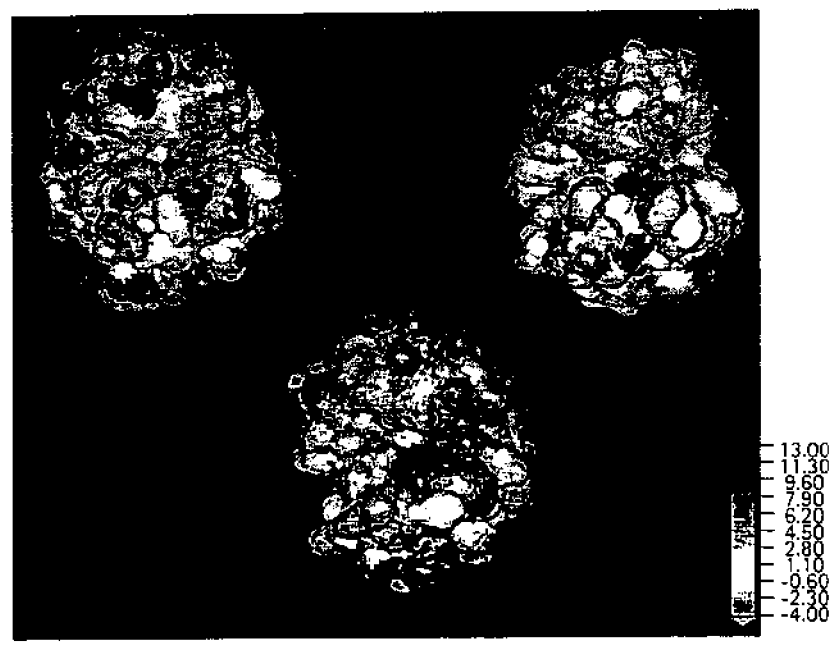
Figure 7C:
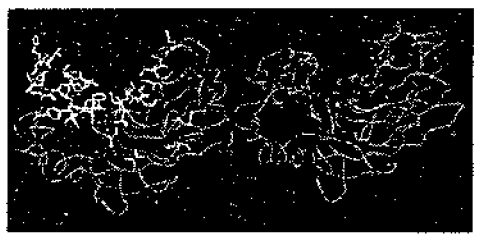
Figure 7D:
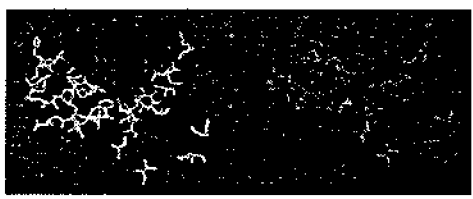
Figure 7E:

FIGS. 7A-7E: Comparisons of the determined structure of MT Cel12A (3B7M) with the known structures of RM Cel12A (1HOB) and TR Cel12A (1OA2). FIG. 7A: Superimposition of the backbones of MT Cel12A (blue), RM Cel12A (red) and TR Cel12A (green) Cel12A. FIG. 7B: Views of the active surface grooves of RM Cel12A (top left), TR Cel12A (top right) and MT Cel12A (bottom middle), color-coded by amino acid polarity. FIG. 7C: Active surface side chains of MT Cel12A (green) and TR Cel12A (blue) superimposed against their backbones (shown as thin ribbons). FIG. 7D: Same active surface side chains shown in panel C, without the backbone (for clarity). FIG. 7E: All-atom surface representations of the side views of MT Cel12A (green), RM Cel12A (red) and TR Cel12A (blue), showing similarities of MT Cel12A with both parent enzymes.

Figure 8A:
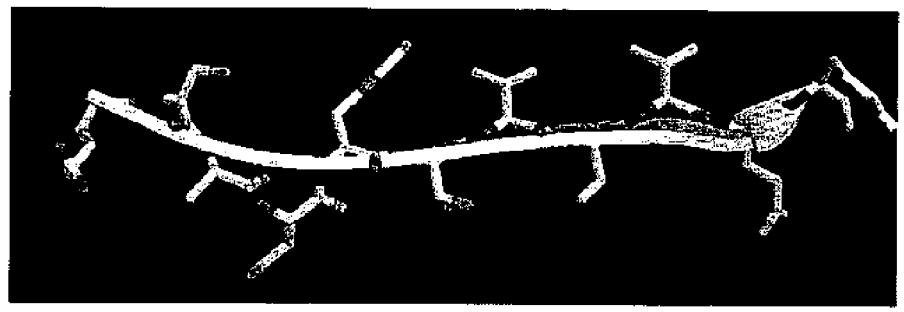
Figure 8B:
Figure 8C:
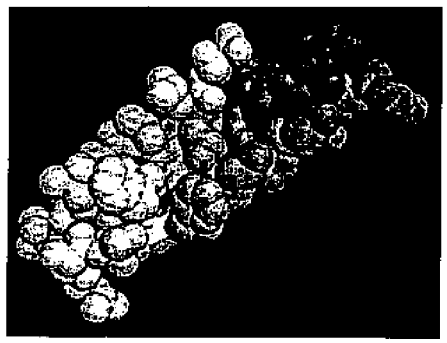
Figure 8D:
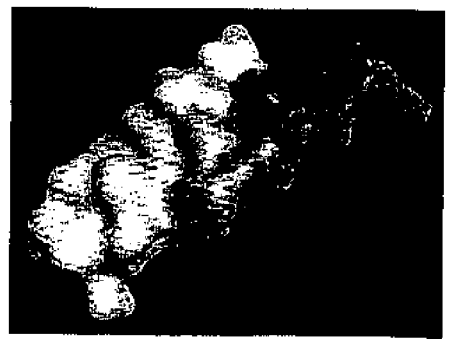

FIGS. 8A-8D: Alternating geometrical disposition of residues within strands participating in beta sheet formation, and the formation of a surface by sidechains from adjoining strands in a sheet. Schematic representations of three strands from RM Cel12A created using the software PYMOL. FIG. 8A: Alternating residues in a strand that is a part of a beta sheet face away from the plane of the sheet in opposite directions. FIG. 8B: Sidechains from adjacent strands in a beta sheet facing away from the sheet in the same direction lie adjacent to each other. FIG. 8C: These atoms of sidechains shown in panel B interact with each other. FIG. 8D: The atoms of sidechains shown in panel C interact well enough to form a surface.

Figure 9A:
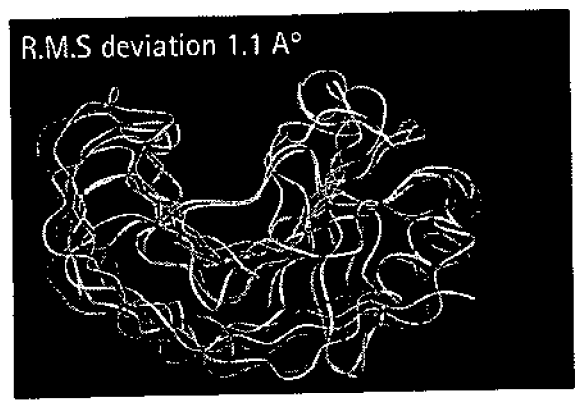
Figure 9B:
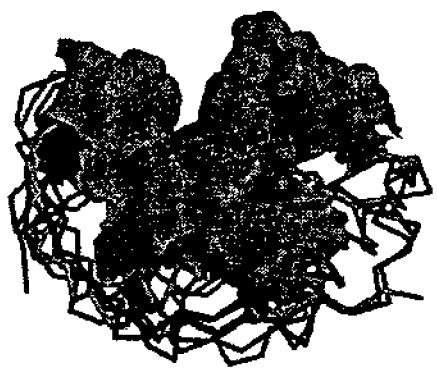
Figure 9C:
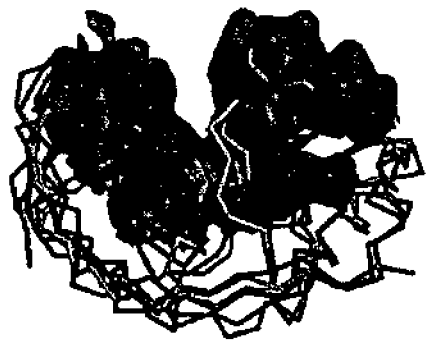

FIGS. 9A-9C: Visual depiction of structural homology between RM & TR Cel12A, and of beta sheets constituting the active surfaces of both enzymes. FIG. 9A: Superposition of backbones. Despite the existence of only ~28% sequence identity between RM Cel12A and TR Cel12A, the structures are highly homologous, and can be superimposed with an RMSD of 1.1 A°. Both proteins consist of two curved beta sheets sandwiched into a beta jellyroll fold, with the cellulose-binding groove positioned in the concave surface of the upper sheet. The RM Cel12A backbone is shown in yellow. It's active surface is shown in cyan. The TR Cel12A backbone is shown in red. FIG. 9B: The active surface of RM Cel12A. Shown over the superimposed backbones of the two proteins is the active surface of RM Cel12A, consisting of residues from the upper beta sheet constituting the cellulose-binding groove. The RM Cel12 backbone is shown in red and the TR Cel12A in blue. FIG. 9C: The active surface of TR Cel12A. Shown over the superimposed backbones of the two proteins is the active surface of TR Cel12A, consisting of residues from the upper beta sheet constituting the cellulose-binding groove. The RM Cel12 backbone is shown in red and the TR Cel12A in blue. A visual comparison of this mesophile active surface with that of the thermophile homolog shows a notional 'cut-away' view of the profundity of the surface-engineering attempted in this work.

Figure 10A:
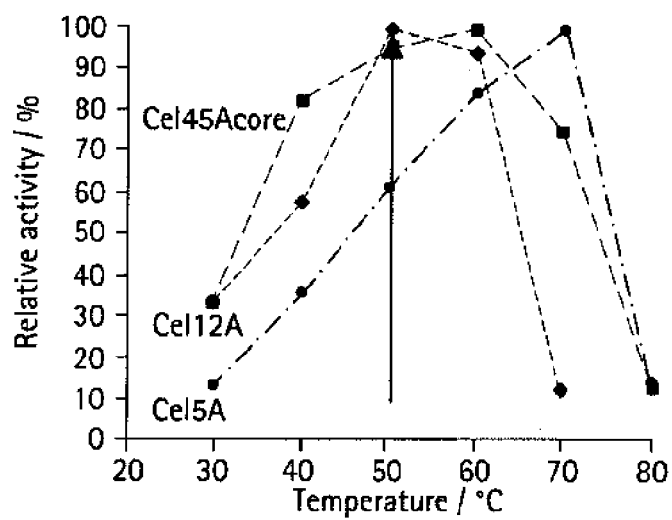
Figure 10B:
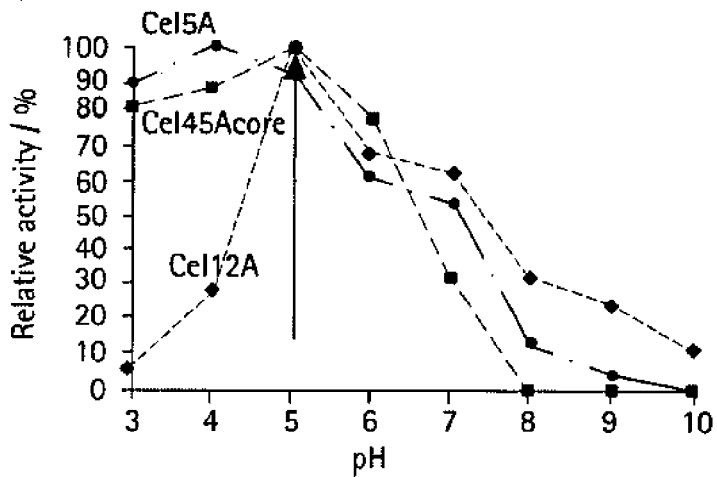
Figure 10C:
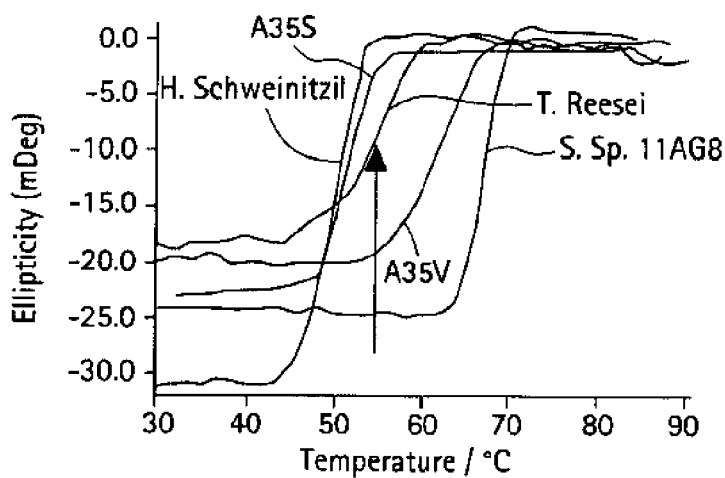

FIGS. 10A-10C: Temperature vs. activity', 'pH vs. activity' and 'temperature vs. structural content' profiles of TR Cel12A. FIGS. 10A and 10B: Variations of TR Cel12A activity with temperature and pH as reported by Karlsson, J., Siika-aho, M., Tenkanen, M. & Tjerneld, F. (2002). *J. Biotechnol.* 99, 63-78. FIG. 10C: Variation of TR Cel12A CD signal (structural content) with temperature as reported by Sandgren, M., Gualfetti, P. J., Shaw, A., Gross, L. S., Saldajeno, M., Day, A. G., Jones, T. A. & Mitchinson, C. (2003). *Protein Science* 12, 848-860. The panels shown in this figure are from the above cited papers.

FIGS. 11A-11C: DNA and Protein sequences of RM Cel12A and MT Cel12A. Top Row—M Cel12A Protein Sequence. Second Row—RM Cel12A DNA Sequence. Third Row—MT Cel12A DNA sequence. Fourth Row—MT Cel12A Protein Sequence. Note: Only residue nos. are shown. Base numbers are not shown. The residue nos. shown are those from the actual sequences in the original references, ignoring gaps. Following the tag, the RM sequence starts with Met (residue 1) which is not shown.

Figure 12:
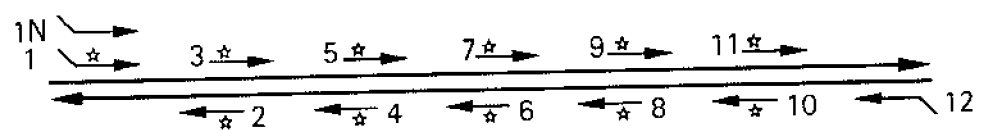

FIG. 12: Schematic diagram of the synthesis of genes encoding RM Cel112A (through PCR from genomic DNA) & MT Cel12A (through SOE-PCR using mutagenic primers). Numbers show assigned primer numbers (see Table 4). Asterisk marks indicate that primers were mutagenic. Mutagenic primers incorporate DNA base changes designed to (i) change RM residues to structurally analogous TR residues, (ii) include loops from TR with no analog in RM, (iii) make silent mutations to optimize PCR feasibility by destroying likelihood of alternative (undesirable) primer-template associations, and (iv) make silent mutations to destroy secondary structure considered likely to affect translation efficiency at the mRNA level, during gene expression. Note: The gene for RM Cel12A was amplified from *R. marinus* genomic DNA using primers 1N and 12. The gene for MT Cel12A was created through splicing of appropriately mutated sections of the gene encoding RM Cel12A, using mutagenic primers 1 through 11, and primer 12 containing no mutations.

Figure 13B:
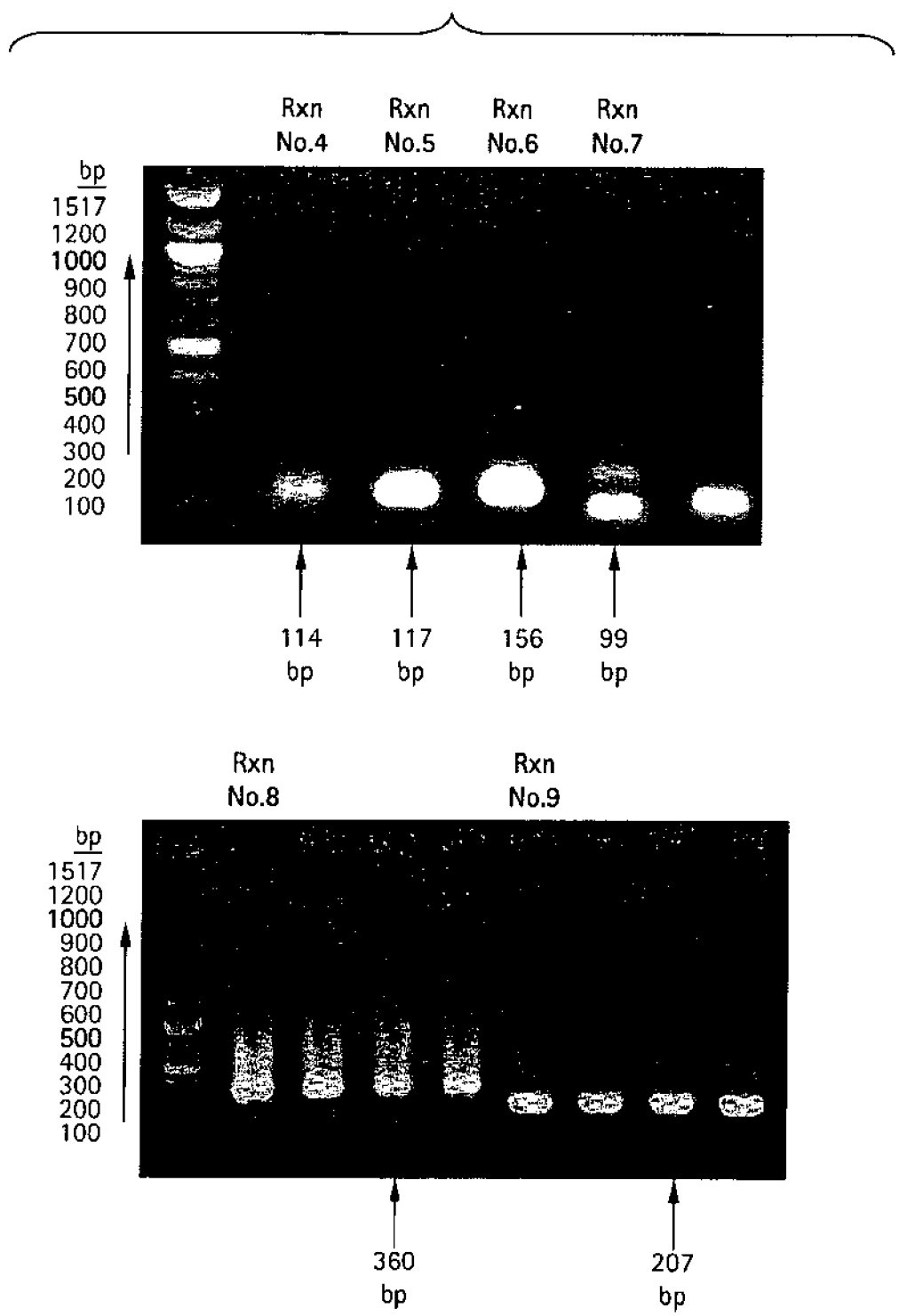

FIGS. 13A-13C: Gels showing amplifications from PCR and SOE-PCR reactions. Gels showing the generation of a) the gene encoding RM Cel12A by PCR from *R. marinus* genomic DNA (Rxn no. 1), and b) the steps involved in the synthesis of the gene encoding MT Cel12A, involving mutagenic PCR amplifications of regions from the gene encoding RM Cel12A, and assembly of such regions through splicing-by-overlap-extension (SOE) PCR (Rxn. Nos. 2-11).

Figure 14A:
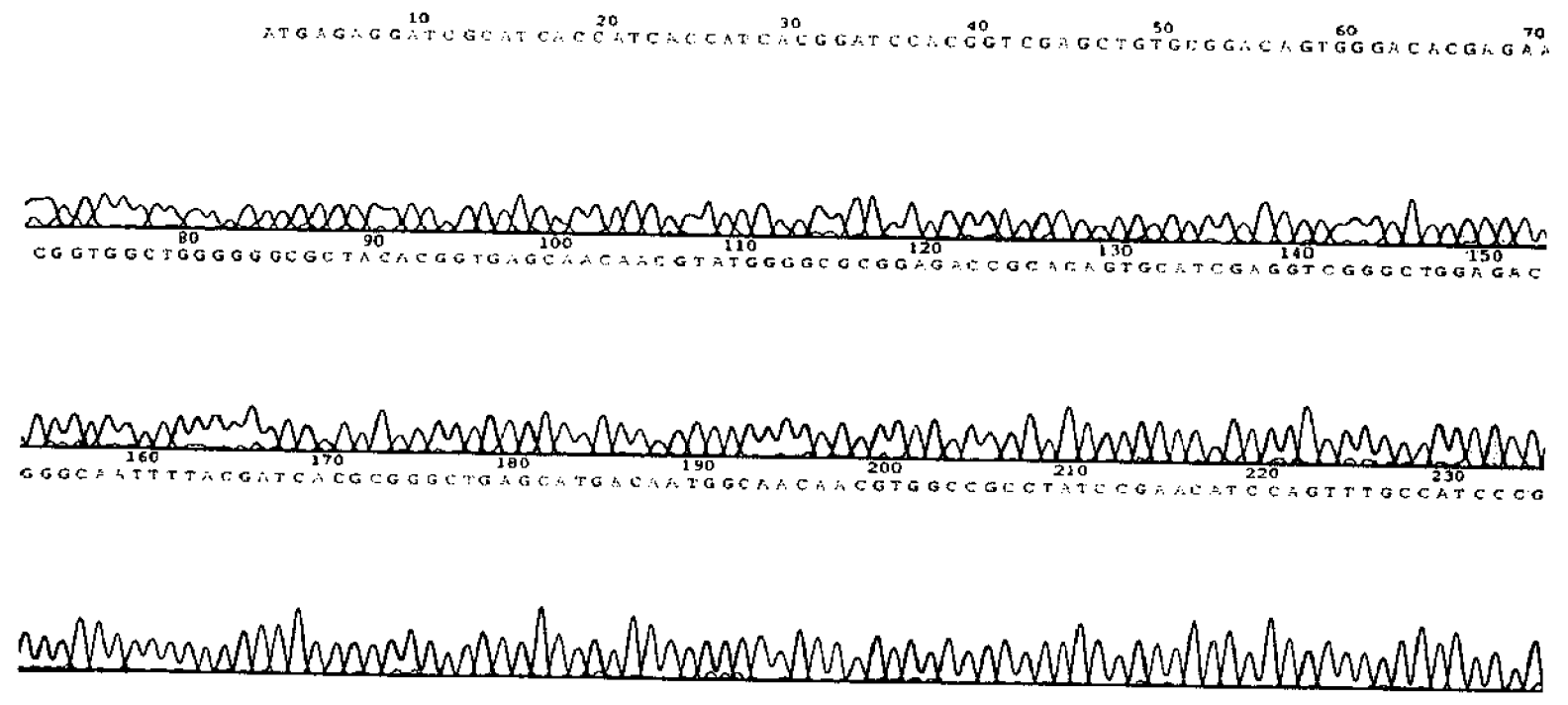
Figure 14B:
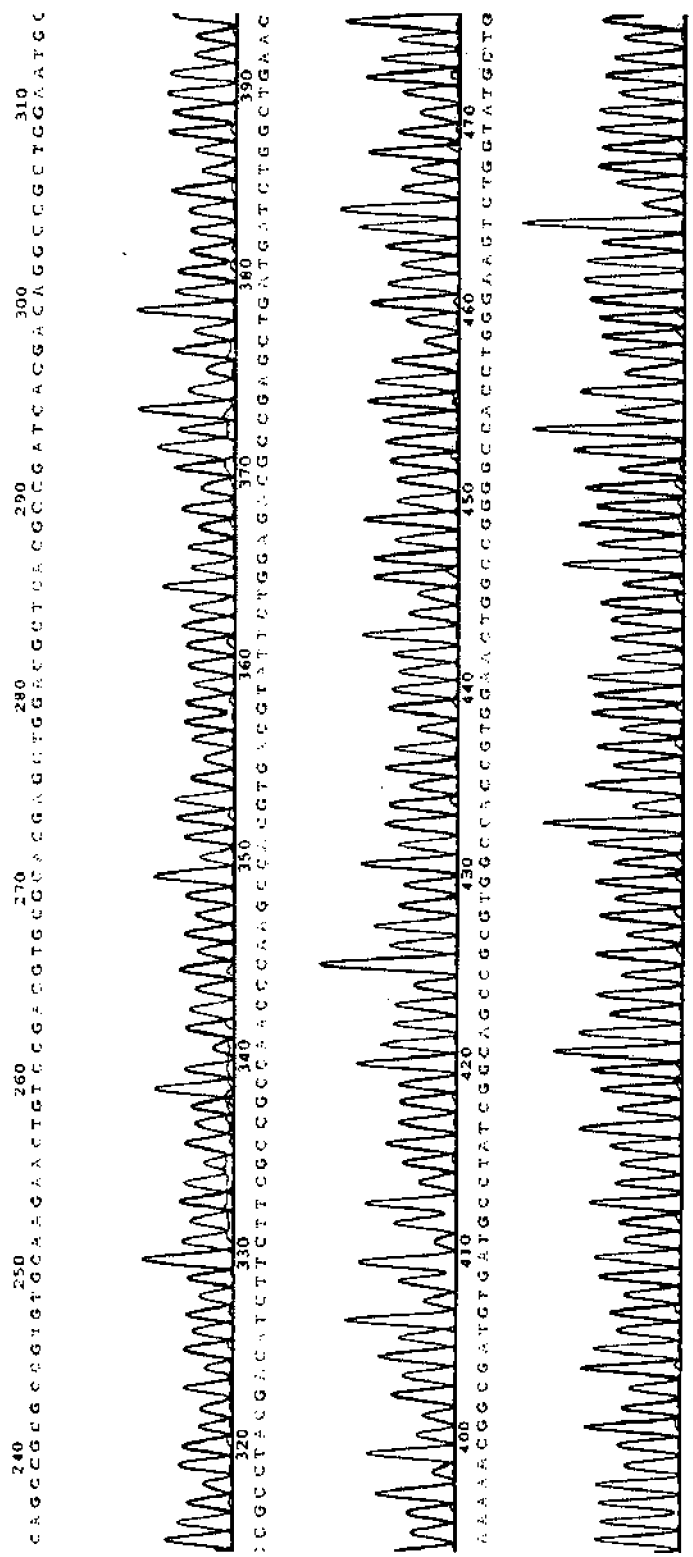
Figure 14C:
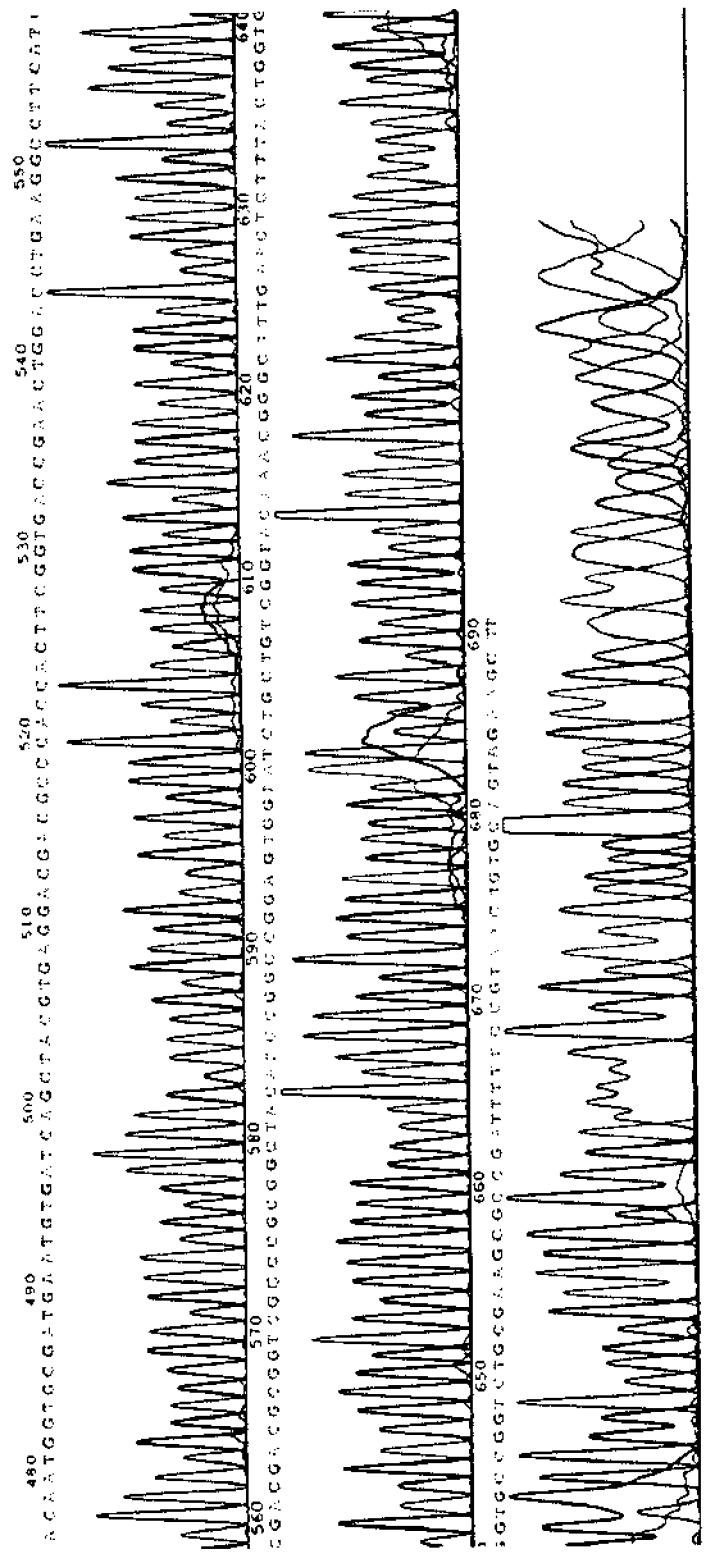

FIGS. 14A-14C: DNA sequencing electrophoretogram confirming the correct construction of the gene encoding MT Cel12A.

Figure 15A:
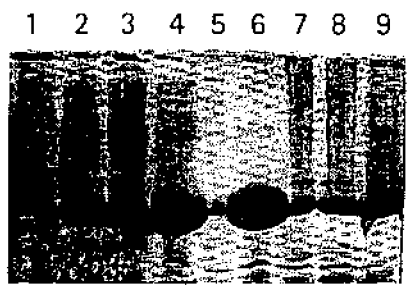
Figure 15B:
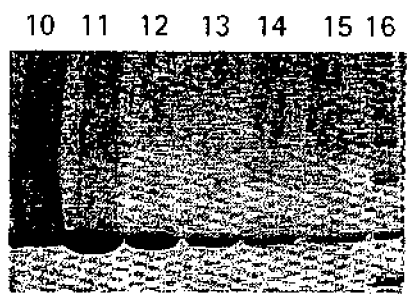
Figure 15C:
Figure 15D:
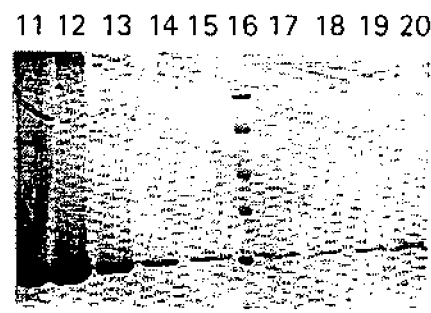

FIGS. 15A-15D: Gels showing non-denaturing purification of MT Cel12A (panels A&B) and RM Cel12A (panels C&D). FIG. 15A: Lane1—Pellet. Lane2—Lysate (in 10 mM Imidazole). Lane3—Flow through. Lane4—Wash (in 20 mM Imidazole). Lane5—Molecular weight marker (From Top to bottom: 116,66,45,35,25,18.4,14.4 kDa respectively). Lane6-9—Eluted MT Cel12A fractions in 1M Imidazole. FIG. 15B: Lanes10-15—Eluted MT Cel12A fractions in 1M Imidazole. Lane 16— Molecular weight marker (From Top to bottom 116,66,45,35,25,18.4 kDa respectively). FIG. 15C: Lane1—Pellet. Lane2—Lysate (in 10 mM Imidazole). Lane3—Flow through. Lane4—Wash (in 20 mM Imidazole). Lane5— Molecular weight marker (From Top to bottom: 116,66,45,35,25,18.4,14.4 kDa respectively). Lane6-9—Eluted MT Cel12A fractions in 1M Imidazole. FIG. 15D: Lanes10-15: Eluted MT Cel12A fractions in 1M Imidazole. Lane 16: Molecular weight marker (From Top to bottom: 116,66,45,35,25,18.4 kDa respectively).

Figure 17A:
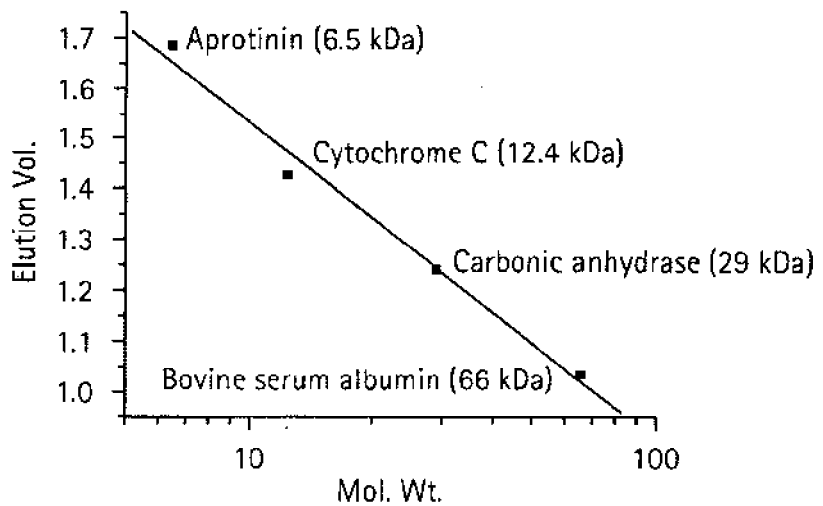
Figure 17B:
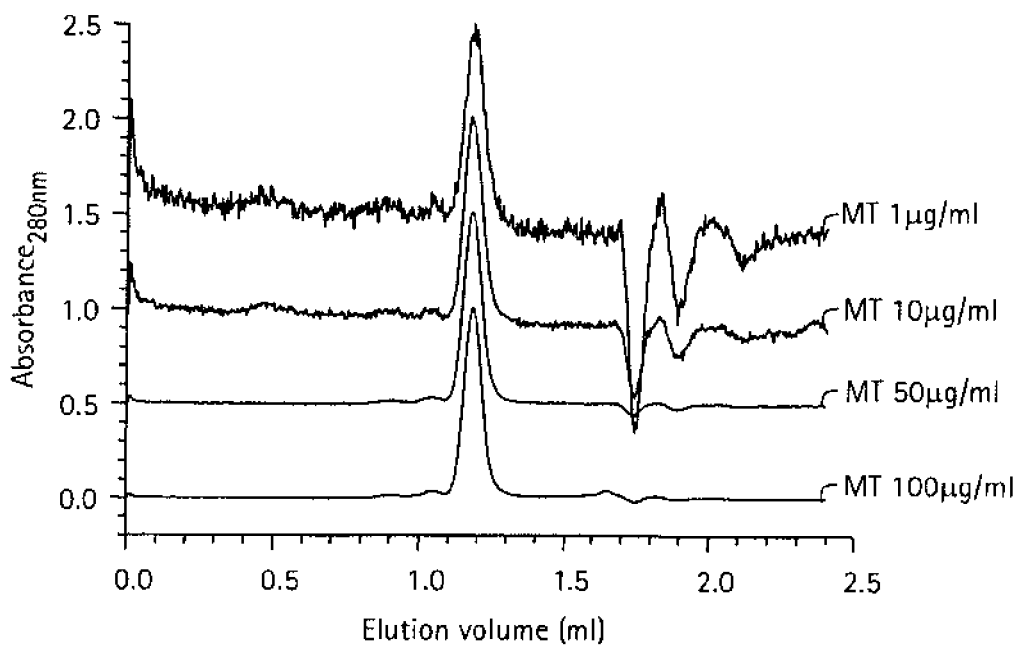

FIG. 16: MS characterization of RM Cel12A and MT Cel12A. Data collected on an ABI Voyager DE-STR MALDI-TOF mass spectrometer, calibrated with IgG, in the linear mode with accuracy >100 ppm. Expected mass of RM Cel12A is 26215.93 Da. Expected mass of MTC Cel12A is 25037.01 Da. Note 1: The observed masses are within the expected range of error for these masses. Note 2: m/z peaks are seen for m values of m=1, z=2 & m=1, z=1 & m=2, z=1 & m=3, FIGS. 17A and 17B: Gel filtration calibration and runs of MT Cel12A at different concentrations. The figure shows stacked gel filtration elution chromatograms of MT Cel12A samples, each of 50 µl volume, loaded after dilution of protein concentration to the values shown in the inset data. The absorbance value ranges were obviously different for the four samples, and so they've been shown stacked here after normalization, to facilitate viewing of changes in elution volume, if any. Samples and the SMART Superdex-75 column were equilibrated with 50 mM Tris pH 8.0. The result observed is that dilution of MT Cel12A does not lead to any changes in gel filtration elution volume (known to be correlated with the molecule's hydnxlynamic volume). The lack of any association, or dissociation, upon dilution, together with the interpolation of its elution volume (1.23 ml) in the calibration plot above, suggests that MT Cel12A is a stable monomer of ~25 kDa.

Table 1: Pairs of analogous residues (with RMSD data) produced by the LSQMAN superimposition program. The table shows only residue pairs for which there was structural superimposition. Non-superimposable loops are not shown above.

Table 2: Details of the active surface transplant. The table shows all pairs of structurally-analogous residues that contribute sidechains to the respective active surface grooves of RM Cel12A and TR Cel12A. Residues constituting beta strands are shown in blocks highlighted in green. Residues that were conserved through the transplant are shown in yellow. Other residues are from loops linking strands, with sidechains facing the solvent. Important note: The above table lists only residues present on the upper sheet and surface loops pointing towards the solvent, and not residues on the upper sheet that point down towards the lower sheet.

Table 3: Gene fragment synthesis & sequence of assembly (PCR and SOE-PCR conditions)

Table 4: Sequences of primers used for gene synthesis

Table 5: Table of discrepancies in sequence information

Table 6: Structural-biochemical and physico-chemical properties of proteins. Properties measured for the meso-active thermo-stable enzyme (MT Cel12A) are shown in a comparative chart together with the properties of the mesophile (TR Cel12A) and thermophile (RM Cel12A) progenitors, known from the literature.

DETAILED DESCRIPTION OF THE INVENTION

The present invention provides a recombinant meso-active thermo-stable protein comprising the structural stability characteristics of a thermophile protein and the activity characteristics of a mesophile protein and its process of synthesis wherein a predominantly non-contiguous set of amino acids comprising the substrate-binding and catalytically-active regions of the surface of the thermophile protein have been replaced by a different non-contiguous set of amino acids occurring at structurally equivalent positions in a structurally-homologous mesophile protein. Our invention proposes to remodel enzyme 'active surfaces'. An enzyme's active surface may be thought to include all residues comprising the active site directly involved in catalysis as well as the residues involved in binding of substrates, or contacting of substrate atoms, at any stage of the enzymatic reaction. What is worthy of note is that even where the structure of an enzyme bound to a substrate-analog is known in atomic detail e.g., through X-ray crystallographic techniques, one can never be confident about which other residues (besides the ones actually seen to be contacting the substrate in the crystal structure) also contact the substrate during enzymatic processing, since many enzymes are thought to change conformation during their binding and catalytic cycles. Thus, given the fact that there is still no way of definitively knowing the complete extent of any enzyme's entire active surface, in practical terms, we shall define the 'active surface' as the entire set of solvent-contacting residues of the particular secondary structural (or supersecondary structural) element within an enzyme which is involved in substrate-binding or catalysis. Thus e.g., if the substrate-binding and catalytic residues are on the solvent-exposed face of a beta sheet-based structure, we shall designate the entire solvent-exposed face of that particular beta sheet at the 'active surface'. This invention proposes and demonstrates a rational methodology for the 'surface remodeling' or 'surface reengineering' of enzyme active surfaces. The remodelling involves comparisons of residue usages by two structurally-homologous enzymes with broadly superimposable backbones ('broadly superimposable' being defined as backbone atom superimposability with a root mean square deviation of 0.5-2.5 Angstroms). Once the comparison is completed, this is followed by a residue-by-residue mutation-based replacement of all the residues comprising one entire active surface in one enzyme with the entire active surface of the other enzyme—an approach that we refer to as 'surface transplantation' because it results in the effective transplantation of an active surface from one enzyme to another enzyme. If the two enzymes are chosen in such a way that they differ in respect of their structural stabilities and optimum conditions for functionality, such an act of 'transplantation' results in the folding-based creation of a novel enzymatic biocatalyst that combines the structural stability features of a 'host' enzyme and the activity characteristics of a 'guest' enzyme, the host and the guest being the two enzymes for which the structural homology comparison was conducted. Thus, the host and guest enzymes effectively become the progenitor enzymes of the novel enzymatic biocatalyst, because the guest enzyme contributes the active surface, and the host enzyme contributes all other residues and the bulk of the novel enzyme's structure.

It is well known that the active site forms as a result of the formation of the enzyme's overall three-dimensional structure, i.e., it is dependent on the enzyme's folding. Since the active site constitutes a subset of the active surface, it follows that the active surface also forms as a result of folding. However, it is important to comprehend that the mere formation of the nearly-correct three-dimensional structure through folding does not imply the correct formation and functioning of the active site, or the 'active surface', of any enzyme. This is because the active site can be sufficiently disturbed structurally to stop functioning, without disturbing the enzyme's overall structure in any discernible manner, as demonstrated by Tsou and coworkers in regard to the unfolding and folding behavior of a number of enzymes for which inactivation can be seen to generally precede global unfolding, suggesting that active sites are conformationally more flexible than the rest of the molecule (Tsou, 1993, *Science* 262, 380-381; Tsou, 1995, *Biochim. Biophys, Acta* 1253, 151-162; Yang and Tsou, 1995, *Biochem J.* 305, 379-384). It follows that the same may be true of active surfaces as well, i.e., the formation and functioning of an active surface may also display some autonomy from the folding of the enzyme which displays that surface. The present invention proposes and demonstrates a rational methodology for verifying and exploiting the autonomy of the active surface from the supporting scaffold of an enzyme's overall three-dimensional structure, by showing how active surfaces may be easily mimicked amongst enzymes through the 'transplantation' effected by multiple (predominantly) non-contiguous residue replacements.

The invention demonstrates the feasibility of active surface transplantation using enzymes with a β jelly-roll fold structure; however, the invention proposes that the specific rational methodology developed and disclosed in this invention may be used to perform such active surface transplantation using any two structurally-homologous enzymes utilizing beta sheet-based active surfaces using backbone atoms superimposable to an RMSD of 0.5-2.5 Angstroms.

Remodeling of the Solvent-Exposed Faces of Beta Skeet Structures

In beta sheet-based proteins such as β jelly-roll fold enzymes, the active surface is formed by β-sheets. One of the thrusts of our invention is that it is possible to mutate the entire beta sheet-based surface of an enzyme taking into consideration the fact that alternate residues on β-strands face away in opposite directions. Those residues which point out of the sheet, towards the solvent, generally form the active surface while those pointing inwards interact hydrophobically with the residues of another sheet, with no interactions between these two sets of residues. Therefore, our case is that it is feasible to remove the solvent-facing set of residues from a beta sheet and replace them by an equivalent solvent-facing set of residues from a structurally-similar (homologous) enzyme, i.e., in other words, to 'notionally transplant' the entire active surface of one enzyme onto another enzyme, either within in a β jelly-roll fold enzyme, as we propose to do here, or indeed in any other beta sheet-based surface that offers the opportunity to separately treat buried residues involved predominantly in determining the enzyme's overall fold and structural stability from those exposed on the protein's surface and participate in its function.

Structural Analyses of Transplantation Feasibility.

Our transplantation approach applies only to beta sheet-based protein structures. Due to the trans configurations of peptide bonds in the extended conformation in beta sheets, the sidechain of any residue in a strand faces away from the sheet in a direction exactly opposite to that of its two immediate neighbors on either side. Alternating sets of residues in a sheet thus face away in opposite directions and evolve entirely independent packing schemes for their sidechains, with little scope for any mutual influence of the two faces on each other. In perfectly planar sheets, residues on the same face can sometimes be too far apart to interact effectively to create a surface; thus, in multi-sheet structures, residues achieve rigid conformations through the stacking together of sheets which allows interactions amongst facing sets of sidechains. Beta sheets made of long strands are, however, rarely perfectly planar, with most curving naturally. Although such curved sheets can also stack (as e.g., occurs between the top and bottom sheets of Cel12A enzymes), residues on the concave, solvent-exposed face of the top sheet in a set of stacked sheets can potentially interact mutually, to create an autonomous packing scheme (FIGS. 1A-1C) and a surface that is effectively insulated away from the other sheets in the stack. This creates possibilities for the selective remodeling of the concave face of the top sheet (FIGS. 1A, 2B). We proceeded to remodel the top sheet forming the active surface of RM Cel12A as detailed below.

RM Cel12A and TR Cel12A share about 28% amino acid sequence identity. A detailed examination of the two structures allowed identification of analogous residue positions in the two proteins. For each pair of analogous residues in either protein, we identified those with backbone atoms participating in strands constituting, or bordering, the cellulose-binding groove, and then separately designated these as having sidechains that: (a) face upwards into the groove, (b) downwards (away from the groove) towards the lower beta sheet, or (c) fall in loop regions separating strands. Residues facing downwards were then removed from the list, as were residues present in loop structures which did not have sidechains participating in groove formation. The remaining residues, together with certain groove-constituting residues in either protein with no counterparts in the other protein, are shown in Table 2, which also summarizes details regarding which residue positions are conserved, and which positions constitute structurally-analogous pairs of residues that are non-identical. In table 2, several sets of sidechains from alternating residue positions can be seen to occur in separate 'blocks' where these derive from the same beta strand, although residues constituting the surface are drawn from all over the protein's sequences (FIG. 2A).

In summary, the groove itself and the elevated regions bordering the groove can be seen to be formed by a total of 66 residues in RM Cel12A, and by 57 residues at structurally-analogous positions in TR Cel12A. Only 29 residues participating in the formation of the active surface of TR Cel12A are represented by a non-identical set of structurally-analogous counterparts in RM Cel12A. Further, two loops of 12 residues (Cys66-Leu77) and 4 residues (Ser115-Gly118), respectively, in RM Cel12A are replaced in TR Cel12A by non-structurally-homologous loops of 3 residues each [(Ile67-Gln69) and (His107-Thr110)]. Also, between the analogous positions in TR Cel12A corresponding to Asp160 and Trp161 in RM Cel12A, there is a residue insertion (Ala153). Therefore (see Table 2), the differences between the active surfaces of RM Cel12A and TR Cel12A are defined by a total of 36 residues from TR Cel12A [29 (analogous)+3 (from one loop)+3 (from another loop)+1 (from an insertion)].

Our engineering objective was thus to replace RM Cel12A residues with TR Cel12A residues at these 36 positions. The sequences of the two enzymes are shown in FIG. 2A, together with the sequence of the redesigned *R. marinus* enzyme incorporating these 36 residue changes which was given the name 'meso-active thermo-stable' Cel12A, or MT Cel12A. The synthesis of the gene encoding MT Cel12A was achieved through multiple mutation-incorporating polymerase chain reaction (PCR) steps, followed by the joining of the obtained amplicons through a step-wise splicing by overlap extension PCR (SOE-PCR) procedure. The gene construct which incorporated a 6×His N-terminal affinity tag was cloned, overexpressed and purified, together with a similar cloning, overexpression and purification of the unmodified RM Cel12A, as a control, with protein masses being confirmed through MALDI-TOF mass spectrometry.

Synthesizing MT Cel12A.

The synthesis of a gene encoding MT Cel12A was achieved through multiple mutation-incorporating polymerase chain reaction (PCR) procedures, followed by assembly of the obtained amplicons through a step-wise splicing by overlap extension PCR (SOE-PCR) procedure [see FIG. 12 (SOE PCR scheme), Table 3 (SOE assembly details), Table 4 (details of primers used), FIG. 13 (PCR results), FIG. 14 (DNA sequence electrophoretogram), and a set of discrepancies in sequence in Table 5]. The gene construct incorporating a 6×His affinity tag was cloned, overexpressed and purified, together with a similar cloning, overexpression and purification of the unmodified *R. marinus* Cel12A (RM Cel12A), as control molecule (FIG. 15). The masses of the two proteins were confirmed through MALDI-TOF mass spectrometry (FIG. 16).

MT Cel12A Folds Like RM Cel12A.

MT Cel12A (FIG. 3A) and RM Cel12A (FIG. 3C) purified through identical procedures under non-denaturing conditions display identical elution volumes, suggestive of a monomeric status, during gel filtration chromatography at pH 8.0. In the presence of salt (100 mM NaCl), and at pH 5.0, MT Cel12A shows identical delays in elution (FIGS. 3A, 3B), indicating possible exposure of hydrophobic residue cluster(s) that interact with the column matrix; such delayed elutions are also seen with RM Cel12A in the presence of salt, and at pH 5.0 (FIGS. 3C, 3D). MT Cel12A chromatographed at four different sample concentrations, spanning three decades of magnitude, eluted at exactly the same elution volume, confirming further that it is a monomer and that it undergoes no association as concentration is raised.

The far-UV circular dichroism spectra of MT Cel12A (FIG. 3E) and RM Cel12A (FIG. 3F) are similar to each other and typical of $\beta_1$ type (beta sheet) secondary structures, with characteristic negative band maxima of comparable signal intensity at 216 nm. Neither enzyme undergoes any alteration of structure upon transfer from acidic to basic pH (FIGS. 3E, 3F). The RM Cel12A spectrum shows an additional negative band in the region of ~225-235 nm which is less distinctly seen in the spectrum of MT Cel12A, suggesting that there may be some minor differences in structure.

MT Cel12A Inherits its $T_m$ from RM Cel12A.

The thermal stabilities of MT Cel12A and RM Cel12A were evaluated by monitoring of reduction in mean residue ellipticity (MRE) as a function of rising temperature between 25 and 98° C. MT Cel12A displayed a $T_m$ of ~93° C., showing complete melting of structure at pH 5.0 (FIG. 4B), and incomplete melting at pH 8.0 (FIG. 4D), thus demonstrating that it possesses a level of structural (thermal) stability comparable to that of RM Cel12A which displayed a $T_m$ of 96° C., showing near-complete melting of structure at pH 8.0 (FIG. 4C), and incomplete melting at pH 5.0 (FIG. 4A). The extreme thermal stability of MT Cel12A clearly owes to its having derived the bulk of its residues, i.e., its entire hydrophobic core and most of its surface, from RM Cel12A which is thermostable. The fact that the two enzymes unfold completely upon heating at two different pH values could probably be rationalized as follows. The high stability available to RM Cel12A at pH 5.0 may not be available to MT Cel12A at this pH because MT Cel12A possesses an active surface evolved to be at its most active (and presumably, therefore, most conformationally flexible) state at pH 5.0; thermal destabilization of this active surface at pH 5.0 probably initiates a melting process that goes to completion. The same argument probably applies to RM Cel12A, which has an active surface evolved to be optimally active at pH 7.0 with comparable activity at pH 8.0 or pH 6.0, but with considerably lower activity at pH 5.0. Thus, each enzyme appears to be more amenable to thermal melting at (or near) the pH of optimal activity of the active surface that it possesses.

MT Cel12A Inherits its $T_{oa}$ from TR Cel12A.

The activities shown by RM Cel12A and MT Cel12A on the substrate, carboxy-methyl cellulose (CMC), measured as a function of temperature at a constant pH of 5.0 (FIG. 5A); as a function of pH at a constant temperature of 50° C. (FIG. 5B); and for different combinations of pH and temperature (FIG. 6), collectively present a number of interesting insights.

Firstly, (a) compared to the $T_{oa}$ of 90° C. shown by RM Cel12A, MT Cel12A has a significantly lowered $T_{oa}$ of 55° C., close to the known $T_{oa}$ of 50° C. shown by TR Cel12A (FIG. 5A). This demonstrates that the active surface of TR Cel12A functions (in MT Cel12A) with its original properties even after transplantation onto the structural scaffold of RM Cel12A, with no upshifting of $T_{oa}$ caused by the availability of a scaffold with a 42° C. higher $T_m$ (i.e., 96° C. instead of 54° C.; see Table 6).

Secondly, (b) despite the $T_{oa}$ of 55° C. shown by MT Cel12A, its activity versus temperature profile (FIG. 5A) is significantly broader than the known corresponding profile for TR Cel12A (FIG. 10). There is substantial retention of activity (e.g., 70% of maximal activity at 70° C., and 7-8% activity at 90° C.) even at high temperatures at which TR Cel12A is known to show no activity, due to the melting of its structure at 54° C. Clearly, therefore, additional stability is imparted to the imported TR Cel12A active surface functioning within MT Cel12A, even though the active surface's $T_{oa}$ remains largely unaltered.

Thirdly, (c) MT Cel12A has a pH of optimal activity that is 1.0 unit lower than that of RM Cel12A, i.e., pH 6.0 instead of 7.0 (FIG. 5B), further establishing the autonomy of the TR Ce12A functioning within MT Cel12A and providing support to the principles underlying their transplantability.

Finally, (d) at pH 5.0 and 50° C., MT Cel12A shows one-fifth the activity of RM Cel12A, (FIG. 6). The value is lower at other temperature and pH values, owing perhaps to the 'fragility' of the transplanted active surface within its new structural context, which may be further improved through mutagenesis. Notwithstanding this, the fact that MT Cel12A is almost one-fifth as active as RM Cel12A at pH 5.0 and 50° C. suggests that the folding and assembly of structural components have occurred nearly perfectly in the new enzyme, from both qualitative and quantitative viewpoints. These results also demonstrate that any microstructural effects (on activity) of the altered scaffold are quite minimal, in comparison to the profundity of the changes introduced.

MT Cel12A Inherits the TR Cel12A Active Surface and the RM Cel12A Scaffold and (Remaining) Surface.

We have determined the structure of MT Cel12A by X-ray crystallography. The structure has been deposited in the protein data bank (PDB) with the identification code (PDB ID) 3B7M. The protein crystallizes as a tetramer. The geometry of the tetramer is such that each subunit interacts with two other subunits. Under the pH and ionic strength conditions used in solution, however, as already mentioned, the molecule is a monomer, with a dimeric population also observed upon storage (data not shown), indicating that the crystallization conditions may have favored the deposition of a dimer of this dimeric form. Detailed views of the monomeric structure are presented in panel A in FIG. 7, which shows a cartoon ribbon diagram of the determined backbone structure of MT Cel12A (blue) superimposed against the known polypeptide backbone structures of RM Cel12A (red) and TR Cel12A (green). The figure reveals that the bulk of the backbone structure of MT Cel12A is like that of RM Cel12A, and TR Cel12A. In panel B in FIG. 7, the surface views of the groove of all three proteins are shown encoded in terms of residue polarity, to demonstrate that the groove of MT Cel12A shares features with that of TR Cel12A. In panel C in FIG. 7, one sees the bulk of sidechains constituting the active surface (in stick form) superimposed upon the backbone ribbons of MT Cel12A (green) and TR Cel12 A (blue), with panel D showing the same sidechains in a somewhat enlarged form, and without the ribbon (for clarity). It is immediately evident that the active surface of MT Cel12A is like that of TR Cel12A, with transplanted residues adopting the same geometry in both cases. In panel E in FIG. 7, the side views of the surfaces of MT Cel12A (green), RM Cel12A (red) and TR Cel12A (blue) are all shown from the same angle. It can be seen that for the most part, the surface of MT Cel12A shares features with RM Cel12A, since most of its residues and all of its surface (barring the active surface groove) are derived from RM Cel12A. In summary, the structural details demonstrate that MT Cel12A has adopted a folded structure much like RM Cel12A, with a surface much like TR Cel12A (except for some minor deviations in loop regions), despite the introduction of 36 non-contiguous mutations. This provides further support to the experimental observations already presented in this invention showing that MT Cel12A has the structural stability of RM Cel12A and the physical activity characteristics of TR Cel12A.

Concluding Discussion

MT Cel12 A is a novel enzyme that blends the functional characteristics of a mesophile parent with the structural characteristics of a thermophile parent by sourcing a non-contiguous set of residues (constituting the solvent-exposed face of a curved beta sheet responsible for substrate binding) from the mesophile and using it to supplant a structurally-analogous set of residues in the thermophile. The provision of a stable structural scaffold does, of course, noticeably enhance the functionality of the transplanted active surface to a significant degree, at high temperatures, despite the carrying over of the original $T_{oa}$ of TR Cel12A into MT Cel12A. The success of the attempted 'active surface transplantation' demonstrates that the linkage of $T_{oa}$ and $T_m$ in enzymes is not obligatory, and shows how protein engineering can be used to dissect and independently assort thermal stability and functionality in enzymes. The remarkable folding and function of such a thoroughly re-engineered enzyme into a form that was amenable to crystallization and structure determination not only demonstrates the autonomy of operation of an enzyme's active surface within the broader context of its overall three-dimensional structure, but also provides a 'proof-of-concept' demonstration for a novel rational approach that can be used over a wider range of enzymes to short-circuit the natural coevolution of enzyme functionality and stability in organisms, with the goal of producing molecules with characteristics that nature would not normally produce.

The present invention is related with the alteration of the functional behaviour of all beta proteins which is carried out using the following steps:

1) Identification of two proteins of differing physical functional characteristics (e.g., optimum temperature of enzymatic function) but identical chemical functional characteristics (i.e., acting on identical substrates), say A and B.
2) Determination of the nature of the engineering transformation desired, and also determination of which protein from amongst A and B is to be considered to be the 'guest' or donor structure, and which the 'host' or acceptor structure [e.g., the host protein would be the one whose structural stability is desired to be retained, e.g., a thermophile protein, and the guest protein would be the one whose functional behavior is desired to be imported onto the host, through surface transplantation involving specific residue changes (determined as given in steps 3 to 6 below) e.g., a mesophile protein].
3) Superimposition of the polypeptide backbones of A and B.
4) Identification of pairs of residues at analogous surface positions in A and B.
5) Identification of subsets of pairs of residues at analogous positions in A and B that are involved in substrate binding.
6) Determination of a table of residue changes to be made (including substitutions, insertions and deletions that are contiguous, or non-contiguous, from strands and loop regions).
7) Creation of a target polypeptide amino acid sequence, to be synthesized (incorporating unchanged, and changed, residues) through splicing by overlap extension (SOE) polymerase chain reaction (PCR), using appropriate mutagenic primers and wild type template regions from the host gene, to produce mutant proteins.
8) DNA sequencing to confirm correct gene synthesis.
9) Cloning, over-expression and purification of mutant and other versions of enzymes using affinity tags (e.g., a 6×His tag for immobilized metal affinity chromatography).
10) Purification of enzyme for biochemical and biophysical characterization.
11) Activity vs. Temperature profiling using standard assays.
12) Activity vs. pH profiling using standard assays.
13) Far-UV CD spectroscopy to determine secondary structure.
14) Thermal melting profile by monitoring of the circular dichroism (CD) signal in the far-UV range.
15) Mass spectrometry to determine the intact enzyme molecular weight.
16) Gel filtration chromatography to determine the quaternary structural status of the protein (i.e., whether monomeric, or multimeric).
17) X-ray crystallography to determine the three-dimensional structure of the enzyme, and confirm whether the intended structural changes have taken place The following examples are given by way of illustration of the present invention and therefore should not be construed to limit the scope of the present invention

EXAMPLES

Example 1

Design of Meso-Active Thermo-Stable (MT) Cel12A

We examined the structural homology between RM Cel12A and TR Cel12A using the software LSQMAN, to calculate the superimposition of backbones. We used the same software to quantitate the level of backbone superimposability (FIG. 1, panel A) and determined that the backbones could be superimposed with an RMSD of 1.1 A° although the surface features of the two proteins are remarkably different (FIG. 1, panel B). The superimposed backbones were used to determine residue numbers at analogous positions in the two enzymes (Table 1). This information was used to generate structural analogy-based alignments of the protein (FIG. 2) and DNA (FIG. 11) sequences of the two enzymes. Visual examination of the structure of the RM Cel12A enzyme was then performed to identify residues constituting the cellulose-binding groove and associated regions around the groove. These were determined to lie in the beta strands and intervening loops constituting the curved upper beta sheet of the protein. The regions of the chain forming the curved beta sheet are defined by the stretches of residues falling in positions 8-29, 53-77, 100-140, 159-167, 200-210, respectively of the RM Cel12A chain. For each residue within the above-mentioned stretches of RM Cel12A, we determined whether the sidechain points up into the cellulose-binding groove, or lines the groove on the side (i.e., with likelihood of interacting with the cellulosic substrate), or lies on the outer side of the walls lining the groove (with no likelihood of interacting with substrate). This constituted a subset of residues constituting the active surface of RM Cel12A, shown in the first column of Table 2. We then examined the corresponding analogous residues in the sequence/structure of TR Cel12A to determine whether or not for each residue in RM Cel12A, the analogous residue in TR Cel12A also participates in the formation of the cellulose-binding surface. We found that for all residues lying in strands and for most residues lying in loops, both constituents of each pair of structurally-analogous residues had the exact same structural disposition, i.e., both either pointed up towards the cellulose-binding surface (the active surface) or down towards the lower beta sheet, or towards the side. Thus, the subset of residues identified to constitute the active surface of RM Cel12A had analogs in TR Cel12A, shown in the second column of Table 2. It may be noted, however, that analogous residue pairs did not exist for all residue positions. In certain regions, loops could not be superimposed. Therefore, the final definition of residue substitutions and insertions also included non-analogous loops of residues, as shown in Table 2. It may be noted that some residues were conserved in the two enzymes. These did not require to be mutated in course of surface transplantation. The structure-based multiple sequence alignment is shown in FIG. 2, panel A, for the protein sequences of RM Cel12A, MT Cel12A, and TR Cel12A.

TABLE 1

| | 1OA2(TR Cel12A) | | | | 1H0B(RM Cel12A) | |
|---|---|---|---|---|---|---|
| Fragment | GLU-A | 4 | <===> | THR-A | 2 @ | 0.86 A |
| | LEU-A | 5 | <===> | SER-A | 3 @ | 1.16 A |
| | CYS-A | 6 | <===> | CYS-A | 4 @ | 1.06 A * |
| | GLY-A | 7 | <===> | ASP-A | 5 @ | 1.06 A |
| | ARG-A | 8 | <===> | GLN-A | 6 @ | 0.76 A |
| | TRP-A | 9 | <===> | TRP-A | 7 @ | 0.95 A * |
| | ASP-A | 10 | <===> | ALA-A | 8 @ | 0.74 A |
| | ALA-A | 11 | <===> | THR-A | 9 @ | 0.19 A |
| | ARG-A | 12 | <===> | PHE-A | 10 @ | 0.36 A |
| | ASP-A | 13 | <===> | THR-A | 11 @ | 0.16 A |
| | VAL-A | 14 | <===> | GLY-A | 12 @ | 2.73 A |
| Fragment | GLY-A | 17 | <===> | ASN-A | 13 @ | 2.65 A |
| | ARG-A | 18 | <===> | GLY-A | 14 @ | 1.47 A |
| | TYR-A | 19 | <===> | TYR-A | 15 @ | 0.66 A * |
| | ARG-A | 20 | <===> | THR-A | 16 @ | 0.32 A |
| | VAL-A | 21 | <===> | VAL-A | 17 @ | 0.37 A * |
| | ILE-A | 22 | <===> | SER-A | 18 @ | 0.35 A |
| | ASN-A | 23 | <===> | ASN-A | 19 @ | 0.27 A * |
| | ASN-A | 24 | <===> | ASN-A | 20 @ | 0.58 A * |
| | VAL-A | 25 | <===> | LEU-A | 21 @ | 0.26 A |
| | TRP-A | 26 | <===> | TRP-A | 22 @ | 0.38 A * |
| | GLY-A | 27 | <===> | GLY-A | 23 @ | 0.66 A * |
| | ALA-A | 28 | <===> | ALA-A | 24 @ | 1.22 A * |
| Fragment | THR-A | 30 | <===> | GLY-A | 29 @ | 3.23 A |
| | ALA-A | 31 | <===> | PHE-A | 30 @ | 1.77 A |
| | GLN-A | 32 | <===> | GLY-A | 31 @ | 1.38 A |
| | CYS-A | 33 | <===> | CYS-A | 32 @ | 1.16 A * |
| | ILE-A | 34 | <===> | VAL-A | 33 @ | 1.58 A |
| | GLU-A | 35 | <===> | THR-A | 34 @ | 1.55 A |
| | VAL-A | 36 | <===> | VAL-A | 35 @ | 1.25 A * |
| | GLY-A | 37 | <===> | VAL-A | 36 @ | 1.49 A |
| Fragment | GLY-A | 41 | <===> | ALA-A | 42 @ | 2.90 A |
| | ASN-A | 42 | <===> | SER-A | 43 @ | 1.57 A |
| | PHE-A | 43 | <===> | TRP-A | 44 @ | 1.60 A |
| | THR-A | 44 | <===> | HIS-A | 45 @ | 1.84 A |
| | ILE-A | 45 | <===> | ALA-A | 46 @ | 2.41 A |
| | THR-A | 46 | <===> | ASP-A | 47 @ | 3.46 A |
| Fragment | ALA-A | 48 | <===> | TRP-A | 48 @ | 1.68 A |
| | ASP-A | 49 | <===> | GLN-A | 49 @ | 2.61 A |
| | HIS-A | 50 | <===> | TRP-A | 50 @ | 1.21 A |
| | ASP-A | 51 | <===> | SER-A | 51 @ | 1.83 A |
| Fragment | ASN-A | 52 | <===> | GLY-A | 53 @ | 2.89 A |
| | GLY-A | 53 | <===> | GLN-A | 54 @ | 0.96 A |
| | ASN-A | 54 | <===> | ASN-A | 55 @ | 0.47 A * |
| | ASN-A | 55 | <===> | ASN-A | 56 @ | 0.75 A * |
| | VAL-A | 56 | <===> | VAL-A | 57 @ | 0.27 A * |
| | ALA-A | 57 | <===> | LYS-A | 58 @ | 0.36 A |
| | ALA-A | 58 | <===> | SER-A | 59 @ | 0.61 A |
| | TYR-A | 59 | <===> | TYR-A | 60 @ | 0.75 A * |
| | PRO-A | 60 | <===> | GLN-A | 61 @ | 0.44 A |
| | ALA-A | 61 | <===> | ASN-A | 62 @ | 0.24 A |
| | ILE-A | 62 | <===> | SER-A | 63 @ | 0.17 A |
| | TYR-A | 63 | <===> | GLN-A | 64 @ | 0.38 A |
| | PHE-A | 64 | <===> | ILE-A | 65 @ | 1.18 A |
| | GLY-A | 65 | <===> | ALA-A | 66 @ | 2.94 A |
| Fragment | PRO-A | 78 | <===> | LYS-A | 70 @ | 1.48 A |
| | ARG-A | 79 | <===> | ARG-A | 71 @ | 0.84 A * |
| | ARG-A | 80 | <===> | THR-A | 72 @ | 0.69 A |
| | VAL-A | 81 | <===> | VAL-A | 73 @ | 1.02 A * |
| | GLN-A | 82 | <===> | ASN-A | 74 @ | 1.84 A |
| | GLU-A | 83 | <===> | SER-A | 75 @ | 0.57 A |
| | LEU-A | 84 | <===> | ILE-A | 76 @ | 1.03 A |
| | SER-A | 85 | <===> | SER-A | 77 @ | 1.18 A * |
| | ASP-A | 86 | <===> | SER-A | 78 @ | 1.24 A |
| | VAL-A | 87 | <===> | MET-A | 79 @ | 1.21 A |
| | ARG-A | 88 | <===> | PRO-A | 80 @ | 0.63 A |
| | THR-A | 89 | <===> | THR-A | 81 @ | 0.41 A * |
| | SER-A | 90 | <===> | THR-A | 82 @ | 0.63 A |
| | TRP-A | 91 | <===> | ALA-A | 83 @ | 0.77 A |
| | THR-A | 92 | <===> | SER-A | 84 @ | 0.69 A |
| | LEU-A | 93 | <===> | TRP-A | 85 @ | 0.84 A |
| | THR-A | 94 | <===> | SER-A | 86 @ | 0.89 A |
| | PRO-A | 95 | <===> | TYR-A | 87 @ | 1.65 A |
| | ILE-A | 96 | <===> | SER-A | 88 @ | 2.05 A |
| Fragment | GLY-A | 99 | <===> | ILE-A | 92 @ | 1.38 A |
| | ARG-A | 100 | <===> | ARG-A | 93 @ | 0.41 A * |
| | TRP-A | 101 | <===> | ALA-A | 94 @ | 0.49 A |
| | ASN-A | 102 | <===> | ASN-A | 95 @ | 0.61 A * |

TABLE 1-continued

| | 1OA2(TR Cel12A) | | | 1H0B(RM Cel12A) | |
|---|---|---|---|---|---|
| | ALA-A | 103 | <===> | VAL-A | 96 @ 0.66 A |
| | ALA-A | 104 | <===> | ALA-A | 97 @ 0.63 A * |
| | TYR-A | 105 | <===> | TYR-A | 98 @ 0.49 A * |
| | ASP-A | 106 | <===> | ASP-A | 99 @ 0.49 A * |
| | ILE-A | 107 | <===> | LEU-A | 100 @ 1.19 A |
| | TRP-A | 108 | <===> | PHE-A | 101 @ 1.26 A |
| | PHE-A | 109 | <===> | THR-A | 102 @ 0.59 A |
| | SER-A | 110 | <===> | ALA-A | 103 @ 0.97 A |
| | PRO-A | 111 | <===> | ALA-A | 104 @ 1.23 A |
| | VAL-A | 112 | <===> | ASN-A | 105 @ 1.36 A |
| | THR-A | 113 | <===> | PRO-A | 106 @ 2.01 A |
| | ASN-A | 114 | <===> | ASN-A | 107 @ 2.50 A* |
| Fragment | GLY-A | 121 | <===> | GLY-A | 113 @ 5.34 A * |
| | GLY-A | 122 | <===> | ASP-A | 114 @ 1.08 A |
| | ALA-A | 123 | <===> | TYR-A | 115 @ 0.69 A |
| | GLU-A | 124 | <===> | GLU-A | 116 @ 0.58 A * |
| | LEU-A | 125 | <===> | LEU-A | 117 @ 0.47 A * |
| | MET-A | 126 | <===> | MET-A | 118 @ 0.43 A * |
| | ILE-A | 127 | <===> | ILE-A | 119 @ 0.47 A * |
| | TRP-A | 128 | <===> | TRP-A | 120 @ 0.71 A * |
| | LEU-A | 129 | <===> | LEU-A | 121 @ 0.81 A * |
| | ASN-A | 130 | <===> | GLY-A | 122 @ 1.08 A |
| | TRP-A | 131 | <===> | LYS-A | 123 @ 1.71 A |
| | ASN-A | 132 | <===> | TYR-A | 124 @ 1.09 A |
| | GLY-A | 133 | <===> | GLY-A | 125 @ 1.31 A * |
| | GLY-A | 134 | <===> | ASP-A | 126 @ 1.62 A |
| | VAL-A | 135 | <===> | ILE-A | 127 @ 1.32 A |
| | MET-A | 136 | <===> | GLY-A | 128 @ 1.19 A |
| | PRO-A | 137 | <===> | PRO-A | 129 @ 1.11 A * |
| | GLY-A | 138 | <===> | ILE-A | 130 @ 1.31 A |
| | GLY-A | 139 | <===> | GLY-A | 131 @ 0.53 A * |
| | SER-A | 140 | <===> | SER-A | 132 @ 0.23 A * |
| | ARG-A | 141 | <===> | SER-A | 133 @ 0.20 A |
| | VAL-A | 142 | <===> | GLN-A | 134 @ 1.20 A |
| | ALA-A | 143 | <===> | GLY-A | 135 @ 2.23 A |
| | THR-A | 144 | <===> | THR-A | 136 @ 1.19 A * |
| | VAL-A | 145 | <===> | VAL-A | 137 @ 0.84 A * |
| | GLU-A | 146 | <===> | ASN-A | 138 @ 1.04 A |
| | LEU-A | 147 | <===> | VAL-A | 139 @ 1.08 A |
| | ALA-A | 148 | <===> | GLY-A | 140 @ 0.48 A |
| | GLY-A | 149 | <===> | GLY-A | 141 @ 1.59 A * |
| | ALA-A | 150 | <===> | GLN-A | 142 @ 0.35 A |
| | THR-A | 151 | <===> | SER-A | 143 @ 0.36 A |
| | TRP-A | 152 | <===> | TRP-A | 144 @ 0.66 A * |
| | GLU-A | 153 | <===> | THR-A | 145 @ 0.63 A |
| | VAL-A | 154 | <===> | LEU-A | 146 @ 0.64 A |
| | TRP-A | 155 | <===> | TYR-A | 147 @ 0.05 A |
| | TYR-A | 156 | <===> | TYR-A | 148 @ 0.25 A * |
| | ALA-A | 157 | <===> | GLY-A | 149 @ 0.47 A |
| | ASP-A | 158 | <===> | TYR-A | 150 @ 2.37 A |
| | TRP-A | 159 | <===> | ASN-A | 151 @ 3.08 A |
| | ASP-A | 160 | <===> | GLY-A | 152 @ 3.40 A |
| Fragment | TRP-A | 161 | <===> | MET-A | 154 @ 1.09 A |
| | ASN-A | 162 | <===> | GLN-A | 155 @ 0.94 A |
| | TYR-A | 163 | <===> | VAL-A | 156 @ 0.36 A |
| | ILE-A | 164 | <===> | TYR-A | 157 @ 0.38 A |
| | ALA-A | 165 | <===> | SER-A | 158 @ 0.22 A |
| | TYR-A | 166 | <===> | PHE-A | 159 @ 0.19 A |
| | ARG-A | 167 | <===> | VAL-A | 160 @ 0.56 A |
| | ARG-A | 168 | <===> | ALA-A | 161 @ 1.13 A |
| | THR-A | 169 | <===> | GLN-A | 162 @ 1.58 A |
| | THR-A | 170 | <===> | THR-A | 163 @ 1.80 A * |
| | PRO-A | 171 | <===> | ASN-A | 164 @ 1.79 A |
| | THR-A | 172 | <===> | THR-A | 165 @ 1.26 A * |
| | THR-A | 173 | <===> | THR-A | 166 @ 0.41 A * |
| | SER-A | 174 | <===> | ASN-A | 167 @ 1.10 A |
| | VAL-A | 175 | <===> | TYR-A | 168 @ 0.85 A |
| | SER-A | 176 | <===> | SER-A | 169 @ 2.29 A * |
| Fragment | LEU-A | 178 | <===> | GLY-A | 170 @ 0.30 A |
| | ASP-A | 179 | <===> | ASP-A | 171 @ 1.89 A * |
| | LEU-A | 180 | <===> | VAL-A | 172 @ 1.14 A |
| | LYS-A | 181 | <===> | LYS-A | 173 @ 0.89 A * |
| | ALA-A | 182 | <===> | ASN-A | 174 @ 0.94 A |
| | PHE-A | 183 | <===> | PHE-A | 175 @ 0.41 A* |
| | ILE-A | 184 | <===> | PHE-A | 176 @ 0.43 A |
| | ASP-A | 185 | <===> | ASN-A | 177 @ 0.66 A |
| | ASP-A | 186 | <===> | TYR-A | 178 @ 1.02 A |
| | ALA-A | 187 | <===> | LEU-A | 179 @ 1.41 A |
| | VAL-A | 188 | <===> | ARG-A | 180 @ 1.78 A |
| | ALA-A | 189 | <===> | ASP-A | 181 @ 2.59 A |
| Fragment | ILE-A | 193 | <===> | TYR-A | 185 @ 3.19 A |
| | ARG-A | 194 | <===> | ASN-A | 186 @ 1.56 A |
| | PRO-A | 195 | <===> | ALA-A | 187 @ 1.95 A |
| Fragment | GLU-A | 196 | <===> | GLY-A | 189 @ 0.61 A |
| | TRP-A | 197 | <===> | GLN-A | 190 @ 0.91 A |
| | TYR-A | 198 | <===> | TYR-A | 191 @ 0.24 A* |
| | LEU-A | 199 | <===> | VAL-A | 192 @ 0.63 A |
| | HIS-A | 200 | <===> | LEU-A | 193 @ 1.25 A |
| | ALA-A | 201 | <===> | SER-A | 194 @ 1.33 A |
| | VAL-A | 202 | <===> | TYR-A | 195 @ 1.02 A |
| | GLU-A | 203 | <===> | GLN-A | 196 @ 0.49 A |
| | THR-A | 204 | <===> | PHE-A | 197 @ 0.43 A |
| | GLY-A | 205 | <===> | GLY-A | 198 @ 0.41 A* |
| | PHE-A | 206 | <===> | THR-A | 199 @ 0.62 A |
| | GLU-A | 207 | <===> | GLU-A | 200 @ 0.53 A* |
| | LEU-A | 208 | <===> | PRO-A | 201 @ 0.55 A |
| | TRP-A | 209 | <===> | PHE-A | 202 @ 0.37 A |
| | GLU-A | 210 | <===> | THR-A | 203 @ 1.06 A |
| | GLY-A | 211 | <===> | GLY-A | 204 @ 2.91 A* |
| Fragment | ALA-A | 213 | <===> | GLY-A | 206 @ 2.82 A |
| | GLY-A | 214 | <===> | THR-A | 207 @ 2.09 A |
| | LEU-A | 215 | <===> | LEU-A | 208 @ 1.58 A* |
| | ARG-A | 216 | <===> | ASN-A | 209 @ 0.77 A |
| | SER-A | 217 | <===> | VAL-A | 210 @ 1.35 A |
| | ALA-A | 218 | <===> | ALA-A | 211 @ 2.55 A* |
| | ASP-A | 219 | <===> | SER-A | 212 @ 1.31 A |
| | PHE-A | 220 | <===> | TRP-A | 213 @ 1.05 A |
| | SER-A | 221 | <===> | THR-A | 214 @ 0.88 A |
| | VAL-A | 222 | <===> | ALA-A | 215 @ 1.04 A |
| | THR-A | 223 | <===> | SER-A | 216 @ 2.12 A |
| | VAL-A | 224 | <===> | ILE-A | 217 @ 1.67 A |
| | GLN-A | 225 | <===> | ASN-A | 218 @ 1.62 A |

TABLE 2

| Original residue in the R. marinus chain | Corresponding (analogous) residue in the T. reesei chain | Structural origin | Action taken |
|---|---|---|---|
| Arg8 | Gln6 | Loop | Mutated |
| Trp9 | Trp7 | Strand | Conserved |
| Ala11 | Thr9 | Strand | Mutated |
| Asp13 | Thr11 | Strand | Mutated |
| Arg20 | Thr16 | Strand | Mutated |
| Ile22 | Ser18 | Strand | Mutated |
| Asn24 | Asn20 | Strand | Conserved |
| Trp26 | Trp22 | Strand | Conserved |
| Asn54 | Asn55 | Loop | Conserved |
| Asp55 (Asn 55 in the reported sequence) | Asn56 | Loop | Mutated |
| Val56 | Val57 | Loop | Conserved |
| Tyr59 | Tyr60 | Strand | Conserved |
| Ala61 | Asn62 | Strand | Mutated |
| Tyr63 | Gln64 | Strand | Mutated |
| Gly65 | Ala66 | Strand | Mutated |
| Cys66-Leu77 i.e., Cys66, His67, Trp68, Gly69, Ala70, Cys71, Thr72, Ser73, Asn74, Ser75, Gly76, Leu77 | Ile67-Gln69 i.e., Ile67, Pro68, Gln69 | Loop, with no structural correspondence between RM and TR sequemces | Mutated |
| Arg100 | Arg93 | Strand | Conserved |
| Asn102 | Asn95 | Strand | Conserved |
| Ala104 | Ala97 | Strand | Conserved |
| Asp106 | Asp99 | Strand | Conserved |
| Trp108 | Phe101 | Strand | Mutated |
| Ser110 | Ala103 | Strand | Mutated |
| Pro111 | Ala104 | Loop | Mutated |
| Gly112 (Val112 in the reported sequence) | Asn105 | Loop | Mutated |

TABLE 2-continued

| Original residue in the R. marinus chain | Corresponding (analogous) residue in the T. reesei chain | Structural origin | Action taken |
|---|---|---|---|
| Thr113 | Pro106 | Loop | Mutated |
| Asn114 | Asn107 | Loop | Conserved |
| Ser115-Gly121 i.e., Ser115, Ser116, Asn117, Gly118, Tyr119, Ser120, Gly121 (Gly116 in the reported sequence) | His108-Asp113 i.e., His108, Val109, Thr110, Tyr111, Ser112, Gly113 | Loop, but with no structural corresp. between RM and TR | Tyr111, Ser112 & Gly113 Conserved; His108, Vs109, and Thr110 Mutated |
| Gly122 | Asp114 | Strand | Mutated |
| Glu124 | Glu116 | Strand | Conserved |
| Met126 | Met118 | Strand | Conserved |
| Trp128 | Trp120 | Strand | Conserved |
| Trp131 | Lys123 | Loop | Mutated |
| Gly134 | Asp126 | Loop | Mutated |
| Gly138 | Ile130 | Loop | Mutated |
| Ser140 | Ser132 | Loop | Conserved |
| Trp159 | Asn151 | Loop | Mutated |
| Asp160 | Gly152 | Loop | Mutated |
| — | Ala153 | Loop | Inserted |
| Trp161 | Met154 | Strand | Mutated |
| Tyr163 | Val156 | Strand | Mutated |
| Ala165 | Ser158 | Strand | Mutated |
| Arg167 | Val160 | Strand | Mutated |
| His200 | Leu193 | Loop | Mutated |
| Ala201 | Ser194 | Strand | Mutated |
| Glu203 | Gln196 | Strand | Mutated |
| Gly205 | Gly198 | Strand | Conserved |
| Glu207 | Glu200 | Strand | Conserved |
| Trp209 | Phe202 | Strand | Mutated |
| Glu210 | Thr203 | Loop | Mutated |

Example 2

Modeling of the Structure of MT Cel12A

A model for the transplanted protein (MT Cel12A) was generated by first generating a coordinate file for MT Cel12A by replacing in silico the coordinates of the residues of RM Cel12A by those of the structurally-analogous residues in TR Cel12A. Atomic bumps and bond angle anomalies were removed by energy minimization using AMBER 8.0 (DRMS 0.01; using steepest descent and conjugate gradient methods). The model is shown in FIG. 2B in an all-atom surface representation, together with similar representations of RM Cel12A and TR Cel12A.

Example 3

Gene Synthesis, Cloning and DNA Sequencing

We created two genes encoding the recombinant form of the naturally-occurring RM Cel12A enzyme, and the recombinant non-naturally-occurring meso-active thermo-stable enzyme, MT Cel12A. The details of the schemes used for the gene syntheses, the primers and conditions used for PCR and splicing-by-overlap extension (SOE) PCR, and the full sequences of the synthesized gene and the encoded amino acid sequence are given, respectively, in FIG. 11, Tables 3 and 4 and FIG. 12, and FIG. 13. It may be noted that the gene syntheses incorporated (i) a Bam HI restriction site (flanked at its 5' end by a 12 basepair overhang, to facilitate digestion) immediately preceding the codon encoding the starting N-terminal residue (threonine) in genes encoding both RM Cel12A and MT Cel12A, (ii) a stop codon following the codon encoding the last, C-terminal residue (glutamine), and (iii) a Hind III restriction site (flanked at its 3' end by a 12 basepair overhang, to facilitate digestion) immediately succeeding the stop codon. The Bam HI and Hind III restriction sites were digested to allow insertion and ligation of the genes into pQE-30 (Qiagen) vectors. Besides a selection marker (ampicillin resistance), the vector provides an inducible promoter, the transcription start site, the translation start site, and an N-terminal affinity tag (N-MRGSHHHHHGS-C) (SEQ ID NO: 4). The bases used in the vector to encode the last two residues of the tag. i.e., G and S, together constitute the Bam HI site, allowing insertion of the synthesized genes. The vector also provides a stop codon after the Hind III site, but we preferred to use a stop codon before the Hind III site, immediately after the C-terminal glutamine, as already mentioned. Transformation of the ligated vectors was done into competent E. coli XL-1 Blue cells bearing the genotype, hsdR17 recA1 lacF' [proAB+lacI$^q$ lacZ Δ15 Tn10 (tet$^r$)]. Selection of clones was done on LB plates containing tetracycline and ampicillin. An Applied Biosystems DNA sequencer (3130 XL analyzer) was used for performing automated DNA sequencing of clones. Plasmids were purified from XL-1 Blue cells using the ABI MiniPrep kit. Thermo-(cycle)-sequencing reactions were performed either with a vector-specific forward primer with the sequence 5'-CGGATAACAATTTCACACAG-3' (SEQ ID NO: 5), which was used to read through the gene regions encoding the N-terminal end of the protein, or a vector-specific reverse primer with the sequence 5'-GTTCTGAG-GTCATTACTGG-3' (SEQ ID NO: 6) which was used to read through the regions encoding the C-terminal ends of the proteins. Reactions used the ABI ready reaction mix (Big Dye Terminator v3.1 cycle sequencing RR-100), with denaturation at 96° C. (5 min) followed by 30 cycles of denaturation at 96° C. (1 min), annealing at 50° C. (1 min), and extension at 60° C. (2 min). Post-reaction cleanup was done through a standard procedure incorporating washes with EDTA and ethanol, prior to loading onto the analyzer. The electrophoretogram showing the sequence of the gene encoding MT Cel12A is provided in FIG. 14.

TABLE 3

| Rxn No. | Forward Primer | Reverse Primer | Template DNA | Annealing Temp./Time | Extension Temp./Time | Product (bp) | Enzyme | Mg$^{2+}$ Conc. (mM) |
|---|---|---|---|---|---|---|---|---|
| 1 | Primer1 N | Primer12 | RM genomic | 60° C.; 2 min | 75° C.; 3 min | 714 | Triple Master | 2.5 |
| 2 | Primer1 | Primer2 | Product of reaction 1 | 55° C.; 2 min | 75° C.; 3 min | 219 | Triple Master | 2.5 |
| 3 | Primer3 | Primer4 | Product of reaction 1 | 55° C.; 2 min | 75° C.; 3 min | 174 | Deep Vent | 4.0 |
| 4 | Primer5 | Primer6 | Product of reaction 1 | 60° C.; 2 min | 75° C.; 3 min | 114 | Triple Master | 2.5 |

TABLE 3-continued

| Rxn No. | Forward Primer | Reverse Primer | Template DNA | Annealing Temp./Time | Extension Temp./Time | Product (bp) | Enzyme | Mg$^{2+}$ Conc. (mM) |
|---|---|---|---|---|---|---|---|---|
| 5 | Primer7 | Primer8 | Product of reaction 1 | 60° C.; 2 min | 75° C.; 3 min | 117 | Triple Master | 2.5 |
| 6 | Primer9 | Primer10 | Product of reaction 1 | 60° C.; 2 min | 75° C.; 3 min | 156 | Triple Master | 2.5 |
| 7 | Primer11 | Primer12 | Product of reaction 1 | 60° C.; 2 min | 75° C.; 3 min | 99 | Triple Master | 2.5 |
| 8 | Primer1 | Primer4 | Products of reactions 2 and 3 | 55° C.; 2 min | 75°; 3 min | 360 | Triple Master | 2.5 |
| 9 | Primer5 | Primer8 | Products of reactions 4 and 5 | 55° C.; 2 min | 75° C.; 3 min | 207 | Triple Master | 2.5 |
| 10 | Primer9 | Primer12 | Products of reactions 6 and 7 | 60° C.; 2 min | 75° C.; 3 min | 234 | Triple Master | 2.5 |
| 11 | Primer1 | Primer12 | Products of reactions 8, 9 and 10 | 60° C.; 2 min | 75° C.; 3 min | 681 | Deep Vent | 2.0 |

TABLE 4

| Primer No. | Primer Sequence |
|---|---|
| Primer 1N | 5'-ACTTATACTATAGGATCCACTGTCGAGCTGTGT TGTAGATGGGACGCGCGC-3' (SEQ ID NO: 7) |
| Primer 1 | 5'-ACTTATACTATCGGATCCACGGTCGAGCTGTGC GGACAGTGGGACACGAGAACGGTGGCTGGGGGCGC TACACGGTGAGCAACAACGTATGGGGC-3' (SEQ ID NO: 8) |
| Primer 2 | 5'-CTGCGGGATGGCAAACTGGATGTTCGGATAGGC GGCCACGTT-3' (SEQ ID NO: 9) |
| Primer 3 | 5'-GCCTATCCGAACATCCAGTTTGCCATCCGCAGC CGCGCCGTGTGCAAGAACTGTCCGACGTG-3' (SEQ ID NO: 10) |
| Primer 4 | 5'-CAGCTCGGCGTCTCCAGAATACGTCACGTGGTT TGGGTTGGCGGCGAAGAAGATGTCGTAGGCGGC-3' (SEQ ID NO: 11) |
| Primer 5 | 5'-CGCTGGAATGCCGCCTACGACATCTTCTTCGCCGCC AACCCAAACCACGTGACGTATTCTGGAGACGCCGAG CTG-3' (SEQ ID NO: 12) |
| Primer 6 | 5'-GATAGGCATCACATCGCCGTTTTGTTCAGCC-3' (SEQ ID NO: 13) |
| Primer 7 | 5'-AAAAACGGCGATGTGATGCCTATCGGCAGCCGC GTGGCCACCG-3' (SEQ ID NO: 14) |
| Primer 8 | 5'-CCTCACGTAGCTGATCACATTCATCGCACCATT GTCAGCATACCAGACTTCCC-3' (SEQ ID NO: 15) |
| Primer 9 | 5'-TGGTATGCTGACAATGGTGCGATGAATGTGATC AGCTACGTGAGGACGACGCCC-3' (SEQ ID NO: 16) |
| Primer 10 | 5'-GCCCGTTTGCACCGACAGCAGATACCACTCCGG-3' (SEQ ID NO: 17) |
| Primer 11 | 5'-CTGCTGTCGGTGCAAACGGGCTTTGAACTCTTT ACTGGTGGTGCCGGTCTGCGAAGCGCC-3' (SEQ ID NO: 18) |
| Primer 12 | 5'-ACTTATACTATCAAGCTTCTACTGCACAGTTAC GGAAAAATCGGC-3' (SEQ ID NO: 19) |

TABLE 5

| Residue in RM Cel12A (reported in PubMed and PDB) | Residue in RM Cel12A (found by us) | Residue in MT Cel12A (used by us) | Residue in TR Cel12A (reported) | Location | Comment |
|---|---|---|---|---|---|
| Asp49 (D) | Glu | Glu | Gln49 | Not part of active surface | As Asp and Glu are both negatively charged, we decided to keep the Glu found in our cloned gene |
| Asn55 (N) | Asp | Mn | Asn56 | Part of active surface | Since the residue is part of the active surface, and the analogous residue in TR Cel12A is Asn, we decided that it should be Asn in MT Cel12A |
| Val112 (V) | Gly | Asn | Asn105 | - Do - | - Do |
| Gly116 (G) | Ser | His | His108 | - Do - | - Do |
| Ser176 (S) | Thr | Thr | Ser169 | Not part of active surface | The authors who reported the original sequence of RM Cel12A corrected Ser176 to Thr176 |

TABLE 5-continued

| Residue in RM Cel12A (reported in PubMed and PDB) | Residue in RM Cel12A (found by us) | Residue in MT Cel12A (used by us) | Residue in TR Cel12A (reported) | Location | Comment |
|---|---|---|---|---|---|
| | | | | | in Wither el al., Appl. Microb. Biotechnol. 55, 578-584 (2001). Since we found Thr at this position, we retained it. It was not changed to Ser because it is not in the active surface. |

Example 4

Protein Expression & Purification

Small-Scale Purification:

Secondary cultures of XL-1 blue cells, set up in a total volume of 2 liters in shake flasks, were grown at 37° C. upto O.D$_{600}$ of ~0.6, and induced with 0.4 mM IPTG. For production of RM Cel12A, cells were harvested 4 hours after induction, but with MT Cel12A we discovered that it was better to harvest after 12 hours to obtain high yields. Harvested cells were lysed and subjected to standard Ni-NTA-based affinity purification under non-denaturing conditions (Qiagen), with the exception that elution was performed with 1M imidazole. The imidazole was later dialysed out, to obtain pure folded protein. Non-denaturing purification PAGE profiles of MT Cel12A are shown in FIGS. 15A and 15B, and of RM Cel12A in FIGS. 15C and 15D.

Large-Scale Purification:

Sonication- or dynamill-based lysis was used for bacterial cells harvested from culture twelve hours after induction, and resuspended in 50 mM NaH$_2$PO$_4$, 300 mM NaCl, pH 8.0. Centrifugation-based removal of cell debris, was followed by addition of ammonium sulfate to the supernatant to a saturation level of eighty percent, with this being followed by centrifugation-based collection of precipitated protein. The precipitated protein was dissolved in 10 mM citrate buffer of pH 5.0, and dialysis was carried out to remove trace amounts of ammonium sulfate. Heating of the re-dissolved protein at 65° C. for 15-30 minutes in citrate buffer was carried out to heat-denature and heat-precipitate all bacterial cytoplasmic proteins in the lysate, other than the RM Cel12A, or MT Cel12A, enzymes present (depending on which of these proteins was being purified). This was followed by centrifugation to remove heat-precipitated protein, leaving pure RM Cel12A or MT Cel12A in the supernatant, distinguishable as a single band in coomassie-stained SDS-PAGE.

Example 5

Mass Spectrometry

Purified RM Cel12A and MT Cel12A were subjected to mass determination on a Voyager DE-STR MALDI-TOF mass spectrometer. The mass values obtained were well within the expected limits of error in determining mass accuracy for these mass ranges. Further details are provided in the legend to FIG. 16.

Example 6

Far-UV CD Spectroscopy

For wavelength scans & temperature (structure melting) scans, CD spectral measurements were made on a Jasco J-810 spectropolarimeter using protein concentrations in the range of 0.1-0.3 mg/ml, using cuvettes of path length 0.1 or 0.2 cm, and scanning raw ellipticity (θ) values in the range of 250 to 195 nm with N$_2$ gas flowing at 6-9 liters per minute. For pH-dependent temperature scans at a fixed wavelength (218 nm), raw observed ellipticity values were converted to fractional unfolding values by considering the θ value at 218 nm at 25° C. to correspond to the completely folded state, and a θ value of zero to correspond to a completely unfolded state. For standard wavelength scans, raw θ values were converted to mean residue ellipticity values using the formula, $[\theta]=\{\theta_{obs}\times 100\times\text{mean residue weight}\}/\{\text{concentration (mg/ml)}\times\text{path length (cm)}\}$. CD results are provided in FIGS. 3 and 4.

Example 7

Gel Filtration Chromatography

A pre-calibrated and appropriately pre-equilibrated micro-analytical Superdex-75 gel filtration column (bed volume 2.4 ml), connected to a SMART chromatographic workstation (Pharmacia), was used to examine the hydrodynamic volume and elution behavior of RM Cel12A and MT Cel12A under normal conditions in buffer of pH 5.0 or pH 8.0, in the presence of different concentrations of salt, and using different protein concentrations. Calibration data is presented in FIG. 17, panel A, and a control showing the lack of any dissociation in MT Cel12A (further supporting monomeric status) is presented in FIG. 17, panel B.

Example 8

Endoglucanase Enzyme Activity Assays

Enzymatic activity was assayed for MT Cel12 A and RM Cel12A by the standard DNS stopping-based method (Miller et al., 1960, Anal. Biochem. 2, 127-132). For total enzyme activity measurements at a variety of temperatures (with fixed pH), or at a variety of pH values (with fixed temperatures), the conditions detailed below were used. Temperature scan (FIG. 5A)—For incubation at each temperature, we used a final MT Cel12A concentration of 0.1 mg/ml and NaCl concentration of 100 mM in pH 5.0 citrate buffer (final concentration 35 mM). The reaction volume was made up to 1 ml with water for each experiment, and to this 1 ml of 1.8% CMC (carboxymethyl cellulose) was added, and the solution incubated for 1 hour. A total of five such experiments were conducted for each temperature. With RM Cel12A, we used a final enzyme concentration of 0.04 mg/ml and NaCl concentration of 100 mM in pH 5.0 citrate buffer (final concentration 35 mM). The reaction volume was similarly made up to 1 ml, and to this 1 ml of 1.8% CMC was added, and the solution incubated for 20 minutes. A total of five such experiments were conducted for each temperature. Different tubes containing 2 ml each were incubated at the following temperatures: 10, 20, 30, 40, 50, 60, 70, 80, and 90° C. Measurements were also made at 100° C. for RM Cel12A. Following incubation, 3 ml of DNS (dinitrosalicylic acid) reagent were added to each tube, and the tubes were boiled for 15 minutes, to generate color through the reaction of the DNS with reducing sugars liberated by the action of the cellulase on the CMC substrate. A control reaction was also incubated without enzyme. Color development was estimated by absorption measurement at 550 nm, and the value for the control (~0.03) was subtracted. A standard calibration plot with glucose was also made to estimate the reducing sugars—but these have not been reported, as the relevant parameter being monitored was relative activity. The highest activity obtained was considered to be 100% and the remaining activities were converted into percentage values of the maximum activity observed. pH scan (FIG. 5B)—For incubation at each pH, we used a final MT Cel12A concentration of 0.1 mg/ml and NaCl concentration of 100 mM in the appropriate buffer (final concentration 35 mM). Reaction volume was made up to 1 ml, and to this 1 ml of 1.8% CMC was added, and the solution incubated for 1 hour at 50° C. A total of five such experiments were conducted for each pH. With RM Cel12A, we used a final enzyme concentration of 0.01 mg/ml and NaCl concentration of 100 mM in the appropriate buffer (final concentration 35 mM) was made up to 1 ml, and to this 1 ml of 1.8% CMC was added, and the solution incubated for 20 minutes at 50° C. A total of five such experiments were conducted for each pH. Different tubes containing 2 ml each of the above mixture at pH values ranging through 3, 4, 5, 6, 7, 8, 9, and 10. For pH ranging from 3.0-6.0, citrate buffer was used. For pH 7.0-9.0, tris buffer was used. For pH 10.0 carbonate/bicarbonate buffer was used. The color development reaction with DNS was done exactly as for the temperature scans above. The highest activity obtained was considered to be 100% and the remaining activities were converted into percentage values of the maximum activity observed. Comparisons of RM and MT Cel12A activities under identical conditions (FIG. 6)—For comparisons, both RM and MT Cel12A were subjected to activity assays under absolutely identical conditions as follows: Both enzymes were taken at the same final concentration (0.1 mg/ml), in the presence of 100 mM NaCl, in either 45 mM citrate buffer (for comparison at pH 5.0) or 45 mM tris buffer (for comparison at pH 8.0), made up to 1 ml, and added to 1.0 ml of 1.8% CMC to make up a total volume of 2 ml. Incubation was done, in triplicate, at two different temperatures of 50° C. and 90° C., for 1 hr each, at both pH values using both enzymes. The color development reaction with DNS was done exactly as for the temperature and pH scans above.

Example 9

Protein Parameters

RM Cel12A. Length: 236 residues (including a 12 residues-long N-terminal affinity tag with the sequence N-MRGSHHHHHHGS-C) (SEQ ID NO: 20). Molecular Weight: 26215.93 Da. Extinction coefficient (280 nm): 92940.1 O.D at 280 nm is equivalent to 0.28 mg/ml. Isoelectric point (pI): 5.53. MT Cel12A. Length: 227 residues (including a 12 residues-long N-terminal affinity tag with the sequence N-MRGSHHHHHHGS-C) (SEQ ID NO: 20). Molecular Weight: 25037.01 Da. Extinction coefficient (280 nm): 56,000.1 O.D at 280 nm is equivalent to 0.45 mg/ml. Isoelectric point (pI): 5.39

TABLE 6

|  | TR Cel12A[@] | RM Cel12A[@] | MT Cel12A |
| --- | --- | --- | --- |
| No. of residues [*] | 218 | 225 [+] | 215 |
| Molecular mass [#] | 23512 Da | 26216 Da [+] | 25037 Da |
| Isoelectric point | 5.56 | 5.53 | 5.59 |
| pH of Opt. Activity | 5.0 | 7.0 | 6.0 |
| $T_m$ | 54° C. | 96° C. | 93° C. |
| $T_{oa}$ | 50° C. | 90° C. | 55° C. |
| $T_{og}$ | 28° C. | 65° C. | Not applicable |

[*] excluding the length of the N-MRGSHHHHHHGS-C (SEQ ID NO: 20) tag present on RM Cel12A and MT Cel12A.
[*] including the mass of the N-MRGSHHHHHHGS-C (SEQ ID NO: 20) tag present on RM Cel12A and MT Cel12A.
[*] our RM Cel12A clone has only 224 residues after the tag, as we've removed the N-terminal methionine.
[@]Details concerning TR Cel12A and RM Cel12A are from published literature, or our data. Details of TR Cel12A from Sandgren et al., 2003. *Protein Science* 12, 848-860; Simmons, 1977, *Second Intl. Mycol. Congress*, Tampa, Fla. pp. 618; Karlsson et al., 2002. *J. Biotechnol.* 99, 63-78. Details of RM Cel12A are from Crennel et al,. 2002. *J. Mol. Biol.* 320, 883-897; Bjornsdottir et al, 2006. Extremophiles 10, 1-16; Hallorsdottiretal, 1998. *Appl. Microbiol. Biotechnol.* 49, 277-284.

Example 10

Structure Determination

The protein was crystallized using a starting protein concentration of approximately 10 mg/ml, under the following conditions, using the hanging drop vapor diffusion method: 0.2 M $NaH_2PO_4 \cdot H_2O$, 20% PEG 3350, pH 4.5. The crystals grew to a size of 0.5×0.4×0.8 mm, in 2 to 3 days at 20° C. Data were collected using a rotating anode X-ray generator (Rigaku UltraX. Japan) and an image plate detector (MARresearch, Germany). The crystals were diffracted to 2.3 Å resolution. Data were reduced and scaled using the HKL suite of programs (Denzo and Scalepack). The structure was determined by molecular replacement method, using RM Cel12A as a model, and MOLREP program as implemented in CCP4. The refinement was carried out using CNS and CCP4. The model was checked on the graphics workstation by calculating the Fourier and difference Fourier maps using Coot program. The model was validated using PROCHECK and WHATCHECK programs, to check for any errors. The model and structure factors are deposited in the protein data bank (PDB ID No. 3B7M).

ADVANTAGES

The design principles elucidated in this invention facilitate the 'transplant' of any active surface based on a beta sheet structure, from any protein/enzyme to a structurally-homologous protein/enzyme, regardless of the level of sequence identity, but in a manner that is critically dependent on the level of superimposability of the backbones of the donor (guest) and acceptor (host) enzymes, especially in the analogous regions in the two enzymes that involve the transplant.

The successful transplant of an enzyme active surface, as demonstrated through this invention, reveals that an enzyme active surface is an autonomous unit of enzyme micro-structure and function that is able to operate largely independently of the structure and stability of the supporting structural scaffold of its host enzyme, inasmuch as the host structure is retained under all conditions supporting active surface function; as such, this finding (and the associated approach) allow researchers to recombine enzyme structural stabilities with protein activity characteristics from two very different domains of life, as shown in this invention.

The present invention demonstrates the first use of a rigorous rational approach to modulate the physical functional characteristics of an enzyme such as e.g., its temperature of optimal activity.

The present invention demonstrates that the differences in the functional characteristics of active sites in enzymes owe significantly to differences in the features (structure/stability/flexibility/chemistry) of the surfaces that bind to the substrate molecule, rather than merely only to the residues directly involved in catalysis.

Whereas the invention demonstrates the principle through use of beta sheet structures, the concept and approach can be extrapolated through careful structural analyses to transplantation of surfaces involving also helical and other structures.

Whereas the invention demonstrates the transplantation of an active surface involving binding and catalytic action on a small molecule substrate, the concept and approach can be extrapolated to protein-protein and protein-small-molecule interactions not involving any catalytic chemical activity.

Whereas the invention demonstrates the transplantation of only a part of the surface of an enzyme, the concept and approach can be extrapolated to whole-surface transplants between enzymes, or between non-enzyme proteins, to combine the structural stability characteristics of the core of one enzyme with the surface characteristics and functionalities of another homologous enzyme, in ways that nature would not ordinarily facilitate.

---

The invention claimed is:

1. A recombinant meso-active thermo-stable enzyme, wherein said recombinant enzyme is a cellulase, xylanase, amylase or a protease,
wherein said recombinant enzyme comprises a mutated beta sheet-based substrate-binding and catalytically active surface,
wherein said mutated active surface comprises a peptide sequence resulting from replacing, within a set of non-contiguous amino acid residues that comprise a beta sheet-based substrate-binding and catalytically active surface of a thermophile recipient enzyme, all the residues that are non-identical at structurally equivalent positions to a corresponding set of non-contiguous amino acid residues that comprise a beta sheet-based substrate-binding and catalytically active surface of a mesophile donor enzyme,
wherein the residues in the active surface of the thermophile recipient enzyme that have been replaced, have been replaced with the residues at the structurally equivalent positions within the active surface of the mesophile donor enzyme,
and wherein said recombinant enzyme comprises the structural stability characteristics of said thermophile enzyme, and the activity characteristics of said mesophile enzyme.

2. The recombinant meso-active thermo-stable protein according to claim 1, wherein the thermophile recipient enzyme and the mesophile donor enzyme comprise the amino acid sequences of SEQ ID NO: 1 and SEQ ID NO: 2, respectively.

3. The recombinant meso-active thermo-stable protein according to claim 1, wherein the recombinant meso-active thermo-stable protein is a biocatalyst.

4. A recombinant meso-active thermo-stable protein that comprises the amino acid sequence of SEQ ID NO: 3.

5. The recombinant meso-active thermo-stable protein according to claim 4, having the additional characteristics of:
   i. a molecular mass of about 20-30 kiloDaltons;
   ii. a length of about 200-300;
   iii. an isoelectric point in the range of between about 4-8;
   iv. a pH of optimal activity in the range of between about 4-8;
   v. a thermo-stability defined by a melting temperature (Tm) of between about 80-95 degrees centigrade, and
   vi. a meso-activity defined by a temperature of optimal activity (TOA) of between about 30-60 degrees centigrade.

* * * * *

SEQUENCE LISTING

<160> NUMBER OF SEQ ID NOS: 34

<210> SEQ ID NO 1
<211> LENGTH: 224
<212> TYPE: PRT
<213> ORGANISM: Rhodothermus marinus

<400> SEQUENCE: 1

```
Thr Val Glu Leu Cys Gly Arg Trp Asp Ala Arg Asp Val Ala Gly Gly
  1               5                  10                  15

Arg Tyr Arg Val Ile Asn Asn Val Trp Gly Ala Glu Thr Ala Gln Cys
             20                  25                  30

Ile Glu Val Gly Leu Glu Thr Gly Asn Phe Thr Ile Thr Arg Ala Glu
         35                  40                  45

His Asp Asn Gly Asn Asp Val Ala Ala Tyr Pro Ala Ile Tyr Phe Gly
     50                  55                  60

Cys His Trp Gly Ala Cys Thr Asn Ser Ser Gly Leu Pro Arg Arg Val
 65                  70                  75                  80

Gln Glu Leu Ser Asp Val Arg Thr Ser Trp Thr Leu Thr Pro Ile Thr
             85                  90                  95

Thr Gly Arg Trp Asn Ala Ala Tyr Asp Ile Trp Phe Ser Pro Gly Thr
            100                 105                 110

Asn Ser Ser Asn Gly Tyr Ser Gly Gly Ala Glu Leu Met Ile Trp Leu
        115                 120                 125

Asn Trp Asn Gly Gly Val Met Pro Gly Gly Ser Arg Val Ala Thr Val
    130                 135                 140

Val Leu Ala Gly Ala Thr Trp Glu Val Trp Tyr Ala Asp Trp Asp Trp
145                 150                 155                 160

Asn Tyr Ile Ala Tyr Arg Arg Thr Thr Pro Thr Thr Ser Val Thr Glu
                165                 170                 175

Leu Asp Leu Lys Ala Phe Ile Asp Asp Ala Val Ala Arg Gly Tyr Ile
            180                 185                 190

Arg Pro Glu Trp Tyr Leu His Ala Val Glu Thr Gly Phe Glu Leu Trp
        195                 200                 205

Glu Gly Gly Ala Gly Leu Arg Ser Ala Asp Phe Ser Val Thr Val Gln
    210                 215                 220
```

<210> SEQ ID NO 2
<211> LENGTH: 218
<212> TYPE: PRT
<213> ORGANISM: Trichoderma reesei

<400> SEQUENCE: 2

```
Glu Thr Ser Cys Asp Gln Trp Ala Thr Phe Thr Gly Asn Gly Tyr Thr
 1               5                  10                  15

Val Ser Asn Asn Leu Trp Gly Ala Ser Ala Gly Ser Gly Phe Gly Cys
            20                  25                  30

Val Thr Val Val Ser Leu Ser Gly Gly Ala Ser Trp His Ala Asp Trp
        35                  40                  45

Gln Trp Ser Gly Gly Gln Asn Asn Val Lys Ser Tyr Gln Asn Ser Gln
50                  55                  60

Ile Ala Ile Pro Gln Lys Arg Thr Val Asn Ser Ile Ser Ser Met Pro
65                  70                  75                  80

Thr Thr Ala Ser Trp Ser Tyr Ser Gly Ser Asn Ile Arg Ala Asn Val
            85                  90                  95

Ala Tyr Asp Leu Phe Thr Ala Ala Asn Pro Asn His Val Thr Tyr Ser
            100                 105                 110

Gly Asp Tyr Glu Leu Met Ile Trp Leu Gly Lys Tyr Gly Asp Ile Gly
            115                 120                 125

Pro Ile Gly Ser Ser Gln Gly Thr Val Asn Val Gly Gly Gln Ser Trp
            130                 135                 140

Thr Leu Tyr Tyr Gly Tyr Asn Gly Ala Met Gln Val Tyr Ser Phe Val
145                 150                 155                 160

Ala Gln Thr Asn Thr Thr Asn Tyr Ser Gly Asp Val Lys Asn Phe Phe
            165                 170                 175

Asn Tyr Leu Arg Asp Asn Lys Gly Tyr Asn Ala Ala Gly Gln Tyr Val
            180                 185                 190

Leu Ser Tyr Gln Phe Gly Thr Glu Pro Phe Thr Gly Ser Gly Thr Leu
            195                 200                 205

Asn Val Ala Ser Trp Thr Ala Ser Ile Asn
            210                 215

<210> SEQ ID NO 3
<211> LENGTH: 215
<212> TYPE: PRT
<213> ORGANISM: Rhodothermus marinus

<400> SEQUENCE: 3

Thr Val Glu Leu Cys Gly Gln Trp Asp Thr Arg Thr Val Ala Gly Gly
 1               5                  10                  15

Arg Tyr Thr Val Ser Asn Asn Val Trp Gly Ala Glu Thr Ala Gln Cys
            20                  25                  30

Ile Glu Val Gly Leu Glu Thr Gly Asn Phe Thr Ile Thr Arg Ala Glu
        35                  40                  45

His Asp Asn Gly Asn Asn Val Ala Ala Tyr Pro Asn Ile Gln Phe Ala
50                  55                  60

Ile Pro Gln Pro Arg Arg Val Gln Glu Leu Ser Asp Val Arg Thr Ser
65                  70                  75                  80

Trp Thr Leu Thr Pro Ile Thr Thr Gly Arg Trp Asn Ala Ala Tyr Asp
            85                  90                  95

Ile Phe Phe Ala Ala Asn Pro Asn His Val Thr Tyr Ser Gly Asp Ala
            100                 105                 110

Glu Leu Met Ile Trp Leu Asn Lys Asn Gly Asp Val Met Pro Ile Gly
            115                 120                 125

Ser Arg Val Ala Thr Val Glu Leu Ala Gly Ala Thr Trp Glu Val Trp
            130                 135                 140

Tyr Ala Asp Asn Gly Ala Met Asn Val Ile Ser Tyr Val Arg Thr Thr
```

```
                    145                 150                 155                 160
Pro Thr Thr Ser Val Thr Glu Leu Asp Leu Lys Ala Phe Ile Asp Asp
                165                 170                 175

Ala Val Ala Arg Gly Tyr Ile Arg Pro Glu Trp Tyr Leu Leu Ser Val
            180                 185                 190

Gln Thr Gly Phe Glu Leu Phe Thr Gly Gly Ala Gly Leu Arg Ser Ala
        195                 200                 205

Asp Phe Ser Val Thr Val Gln
    210                 215

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Arg Gly Ser His His His His Gly Ser
 1               5                  10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggataacaa tttcacacag                                                      20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttctgaggt cattactgg                                                       19

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acttatacta taggatccac tgtcgagctg tgttgtagat gggacgcgcg c                   51

<210> SEQ ID NO 8
<211> LENGTH: 96
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acttatacta tcggatccac ggtcgagctg tgcggacagt gggacacgag aacggtggct          60
```

```
gggggcgct acacggtgag caacaacgta tggggc                              96
```

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ctgcgggatg gcaaactgga tgttcggata ggcggccacg tt                      42
```

<210> SEQ ID NO 10
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gcctatccga acatccagtt tgccatccgc agccgcgccg tgtgcaagaa ctgtccgacg   60
tg                                                                  62
```

<210> SEQ ID NO 11
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
cagctcggcg tctccagaat acgtcacgtg gtttggttg gcggcgaaga agatgtcgta    60
ggcggc                                                              66
```

<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
cgctggaatg ccgcctacga catcttcttc gccgccaacc caaaccacgt gacgtattct   60
ggagacgccg agctg                                                    75
```

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gataggcatc acatcgccgt ttttgttcag cc                                 32
```

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaaacggcg atgtgatgcc tatcggcagc cgcgtggcca ccg                43

<210> SEQ ID NO 15
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cctcacgtag ctgatcacat tcatcgcacc attgtcagca taccagactt ccc    53

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggtatgctg acaatggtgc gatgaatgtg atcagctacg tgaggacgac gccc   54

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcccgtttgc accgacagca gataccactc cgg                          33

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgctgtcgg tgcaaacggg ctttgaactc tttactggtg gtgccggtct gcgaagcgcc  60

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acttatacta tcaagcttct actgcacagt tacggaaaaa tcggc             45

<210> SEQ ID NO 20
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 20

Met Arg Gly Ser His His His His His His Gly Ser
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 21

His His His His His His
1               5

<210> SEQ ID NO 22
<211> LENGTH: 11
<212> TYPE: PRT
<213> ORGANISM: Rhodothermus marinus

<400> SEQUENCE: 22

Glu Leu Cys Gly Arg Trp Asp Ala Arg Asp Val
1               5                   10

<210> SEQ ID NO 23
<211> LENGTH: 12
<212> TYPE: PRT
<213> ORGANISM: Rhodothermus marinus

<400> SEQUENCE: 23

Gly Arg Tyr Arg Val Ile Asn Asn Val Trp Gly Ala
1               5                   10

<210> SEQ ID NO 24
<211> LENGTH: 8
<212> TYPE: PRT
<213> ORGANISM: Rhodothermus marinus

<400> SEQUENCE: 24

Thr Ala Gln Cys Ile Glu Val Gly
1               5

<210> SEQ ID NO 25
<211> LENGTH: 6
<212> TYPE: PRT
<213> ORGANISM: Rhodothermus marinus

<400> SEQUENCE: 25

Gly Asn Phe Thr Ile Thr
1               5

<210> SEQ ID NO 26
<211> LENGTH: 4
<212> TYPE: PRT
<213> ORGANISM: Rhodothermus marinus

<400> SEQUENCE: 26

Ala Asp His Asp
1

<210> SEQ ID NO 27
```

```
<211> LENGTH: 14
<212> TYPE: PRT
<213> ORGANISM: Rhodothermus marinus

<400> SEQUENCE: 27

Asn Gly Asn Asn Val Ala Ala Tyr Pro Ala Ile Tyr Phe Gly
 1               5                  10

<210> SEQ ID NO 28
<211> LENGTH: 19
<212> TYPE: PRT
<213> ORGANISM: Rhodothermus marinus

<400> SEQUENCE: 28

Pro Arg Arg Val Gln Glu Leu Ser Asp Val Arg Thr Ser Trp Thr Leu
 1               5                  10                  15

Thr Pro Ile

<210> SEQ ID NO 29
<211> LENGTH: 16
<212> TYPE: PRT
<213> ORGANISM: Rhodothermus marinus

<400> SEQUENCE: 29

Gly Arg Trp Asn Ala Ala Tyr Asp Ile Trp Phe Ser Pro Val Thr Asn
 1               5                  10                  15

<210> SEQ ID NO 30
<211> LENGTH: 40
<212> TYPE: PRT
<213> ORGANISM: Rhodothermus marinus

<400> SEQUENCE: 30

Gly Gly Ala Glu Leu Met Ile Trp Leu Asn Trp Asn Gly Gly Val Met
 1               5                  10                  15

Pro Gly Gly Ser Arg Val Ala Thr Val Glu Leu Ala Gly Ala Thr Trp
            20                  25                  30

Glu Val Trp Tyr Ala Asp Trp Asp
        35                  40

<210> SEQ ID NO 31
<211> LENGTH: 16
<212> TYPE: PRT
<213> ORGANISM: Rhodothermus marinus

<400> SEQUENCE: 31

Trp Asn Tyr Ile Ala Tyr Arg Arg Thr Thr Pro Thr Thr Ser Val Ser
 1               5                  10                  15

<210> SEQ ID NO 32
<211> LENGTH: 12
<212> TYPE: PRT
<213> ORGANISM: Rhodothermus marinus

<400> SEQUENCE: 32

Leu Asp Leu Lys Ala Phe Ile Asp Asp Ala Val Ala
 1               5                  10

<210> SEQ ID NO 33
<211> LENGTH: 16
<212> TYPE: PRT
<213> ORGANISM: Rhodothermus marinus

<400> SEQUENCE: 33
```

```
Glu Trp Tyr Leu His Ala Val Glu Thr Gly Phe Glu Leu Trp Glu Gly
  1               5                  10                  15

<210> SEQ ID NO 34
<211> LENGTH: 13
<212> TYPE: PRT
<213> ORGANISM: Rhodothermus marinus

<400> SEQUENCE: 34

Ala Gly Leu Arg Ser Ala Asp Phe Ser Val Thr Val Gln
  1               5                  10
```